US008003786B2

(12) United States Patent
Hoffmann et al.

(10) Patent No.: US 8,003,786 B2
(45) Date of Patent: Aug. 23, 2011

(54) DIHYDROPTERIDINONE COMPOUNDS

(75) Inventors: Matthias Hoffmann, Mittelbiberach (DE); Matthias Grauert, Biberach (DE); Martin Steegmaier, Reutlingen (DE); Anke Baum, Vienna (AT); Jens Juergen Quant, Perchtoldsdorf (AT); Flavio Solca, Vienna (AT); Florian Colbatzky, Stafflangen (DE); Gisela Schnapp, Biberach-Rindenmoos (DE)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 0 days.

(21) Appl. No.: 12/873,687

(22) Filed: Sep. 1, 2010

(65) Prior Publication Data

US 2010/0324288 A1 Dec. 23, 2010

Related U.S. Application Data

(60) Continuation of application No. 12/129,728, filed on May 30, 2008, now Pat. No. 7,816,530, which is a division of application No. 11/219,945, filed on Sep. 6, 2005, now Pat. No. 7,786,299, which is a continuation of application No. 10/903,807, filed on Jul. 30, 2004, now abandoned, which is a continuation of application No. 10/374,876, filed on Feb. 26, 2003, now Pat. No. 6,861,422.

(51) Int. Cl.
*C07D 475/00* (2006.01)
(52) U.S. Cl. ....................................................... 544/261
(58) Field of Classification Search .................. 544/258, 544/261
See application file for complete search history.

(56) References Cited

U.S. PATENT DOCUMENTS

| | | | |
|---|---|---|---|
| 4,957,922 A | 9/1990 | Lammens et al. | |
| 5,167,949 A | 12/1992 | Ferrand et al. | |
| 5,198,547 A | 3/1993 | Bailey et al. | |
| 5,424,311 A | 6/1995 | Billhardt-Troughton et al. | |
| 5,698,556 A | 12/1997 | Chan | |
| 6,096,924 A | 8/2000 | Studer et al. | |
| 6,156,766 A | 12/2000 | Arita et al. | |
| 6,174,895 B1 | 1/2001 | Kleinman | |
| 6,605,255 B2 | 8/2003 | Kroll et al. | |
| 6,806,272 B2 * | 10/2004 | Bauer et al. | 514/250 |
| 6,861,422 B2 * | 3/2005 | Hoffmann et al. | 514/228.5 |
| 6,875,868 B2 | 4/2005 | Bonnert et al. | |
| 7,238,807 B2 | 7/2007 | Duran et al. | |
| 7,241,889 B2 | 7/2007 | Hoffmann et al. | |
| 7,332,491 B2 | 2/2008 | Grauert et al. | |
| 7,371,753 B2 | 5/2008 | Stadtmueller et al. | |
| 7,414,053 B2 | 8/2008 | Grauert et al. | |
| 7,439,358 B2 | 10/2008 | Linz et al. | |
| 7,547,780 B2 | 6/2009 | Grauert et al. | |
| 7,625,899 B2 | 12/2009 | Hoffmann et al. | |
| 7,626,019 B2 | 12/2009 | Duran et al. | |
| 7,629,460 B2 | 12/2009 | Grauert et al. | |
| 7,700,769 B2 | 4/2010 | Grauert et al. | |
| 7,723,517 B2 | 5/2010 | Grauert et al. | |
| 7,728,134 B2 | 6/2010 | Linz et al. | |
| 7,750,152 B2 | 7/2010 | Hoffman et al. | |
| 7,759,347 B2 | 7/2010 | Hoffmann et al. | |
| 7,759,485 B2 | 7/2010 | Linz et al. | |
| 7,807,831 B2 | 10/2010 | Grauert et al. | |
| 7,816,530 B2 | 10/2010 | Grauert | |
| 2002/0183292 A1 | 12/2002 | Pairet et al. | |
| 2002/0183293 A1 | 12/2002 | Banerjee et al. | |
| 2003/0130286 A1 | 7/2003 | Denny et al. | |

(Continued)

FOREIGN PATENT DOCUMENTS

| | | |
|---|---|---|
| CA | 2458699 A1 | 3/2003 |
| CA | 2517020 A1 | 9/2004 |
| CA | 2517010 A1 | 11/2004 |
| CA | 2576290 A1 | 2/2006 |
| EP | 143478 A1 | 6/1985 |
| EP | 347146 A2 | 12/1989 |
| EP | 399856 A1 | 11/1990 |
| EP | 429149 A1 | 5/1991 |
| ES | 2287583 | 12/2007 |
| RU | 2002125451 A | 1/2004 |

(Continued)

OTHER PUBLICATIONS

Tenbrink, R. E. et al., "Antagonist, partial agonist, and full agonist imidazo[1,5-a]quinoxaline amides and carbamates acting through the BABA/Benzodiazepine receptor". J. Med. Chem. 1994, 37, pp. 758-768.

(Continued)

*Primary Examiner* — Andrew D Kosar
*Assistant Examiner* — Erich Leeser
(74) *Attorney, Agent, or Firm* — Michael P. Morris; Anthony P. Bottino

(57) ABSTRACT

Disclosed are new dihydropteridinones of general formula (I)

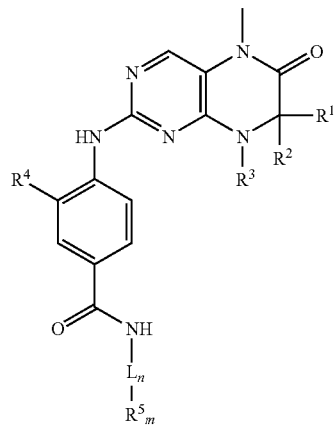

wherein the groups L and $R^1$-$R^5$ have the meanings given in the claims and specification, the isomers thereof, intermediates and processes for preparing these dihydropteridinones and the use thereof as pharmaceutical compositions.

1 Claim, No Drawings

U.S. PATENT DOCUMENTS

| | | |
|---|---|---|
| 2004/0029885 A1 | 2/2004 | Bauer et al. |
| 2004/0147524 A1 | 7/2004 | Bauer et al. |
| 2004/0176380 A1 | 9/2004 | Hoffmann et al. |
| 2005/0014760 A1 | 1/2005 | Hoffmann et al. |
| 2005/0014761 A1 | 1/2005 | Hoffmann et al. |
| 2005/0148501 A1 | 7/2005 | Palmer et al. |
| 2005/0159414 A1 | 7/2005 | Nickolaus et al. |
| 2005/0165010 A1 | 7/2005 | Nickolaus et al. |
| 2006/0004014 A1 | 1/2006 | Hoffmann et al. |
| 2006/0009457 A1 | 1/2006 | Hoffmann et al. |
| 2006/0025411 A1 | 2/2006 | Hoffmann et al. |
| 2006/0035902 A1 | 2/2006 | Linz et al. |
| 2006/0035903 A1 | 2/2006 | Mohr et al. |
| 2006/0046989 A1 | 3/2006 | Grauert et al. |
| 2006/0047118 A1 | 3/2006 | Stadtmueller et al. |
| 2006/0052383 A1 | 3/2006 | Grauert et al. |
| 2006/0058311 A1 | 3/2006 | Munzert et al. |
| 2006/0074088 A1 | 4/2006 | Munzert et al. |
| 2006/0079503 A1 | 4/2006 | Schwede et al. |
| 2007/0208027 A1 | 9/2007 | Duran et al. |
| 2007/0213528 A1 | 9/2007 | Duran et al. |
| 2007/0213529 A1 | 9/2007 | Duran et al. |
| 2007/0213530 A1 | 9/2007 | Duran et al. |
| 2007/0213531 A1 | 9/2007 | Duran et al. |
| 2007/0213534 A1 | 9/2007 | Duran et al. |
| 2007/0219369 A1 | 9/2007 | Duran et al. |
| 2008/0108812 A1 | 5/2008 | Grauert et al. |
| 2008/0113992 A1 | 5/2008 | Grauert et al. |
| 2008/0171747 A1 | 7/2008 | Hoffman et al. |
| 2008/0177066 A1 | 7/2008 | Linz et al. |
| 2008/0194818 A1 | 8/2008 | Grauert et al. |
| 2008/0221099 A1 | 9/2008 | Munzert et al. |
| 2008/0293944 A1 | 11/2008 | Hoffmann et al. |
| 2008/0319190 A1 | 12/2008 | Grauert et al. |
| 2008/0319192 A1 | 12/2008 | Grauert et al. |
| 2008/0319193 A1 | 12/2008 | Grauert et al. |
| 2009/0018333 A1 | 1/2009 | Grauert et al. |
| 2009/0023733 A1 | 1/2009 | Cage et al. |
| 2009/0030004 A1 | 1/2009 | Linz et al. |
| 2009/0124628 A1 | 5/2009 | Hoffmann et al. |
| 2009/0143379 A1 | 6/2009 | Mohr et al. |
| 2009/0238828 A1 | 9/2009 | Munzert et al. |
| 2009/0280115 A1 | 11/2009 | Maier et al. |
| 2009/0298840 A1 | 12/2009 | Linz et al. |
| 2010/0249412 A1 | 9/2010 | Linz et al. |
| 2010/0249458 A1 | 9/2010 | Linz et al. |
| 2010/0280037 A1 | 11/2010 | Linz et al. |
| 2010/0324288 A1 | 12/2010 | Hoffmann et al. |

FOREIGN PATENT DOCUMENTS

| | | | |
|---|---|---|---|
| WO | 9609045 | A1 | 3/1996 |
| WO | 9634867 | A1 | 11/1996 |
| WO | 9636597 | A1 | 11/1996 |
| WO | 9811893 | A1 | 3/1998 |
| WO | 0119825 | A1 | 3/2001 |
| WO | 0170741 | A1 | 9/2001 |
| WO | 0178732 | A1 | 10/2001 |
| WO | 02057261 | A2 | 7/2002 |
| WO | 02076954 | A1 | 10/2002 |
| WO | 02076985 | A1 | 10/2002 |
| WO | 03020722 | A1 | 3/2003 |
| WO | 03093249 | A1 | 11/2003 |
| WO | 2004014899 | A1 | 2/2004 |
| WO | 2004076454 | A1 | 9/2004 |
| WO | 2004093848 | A2 | 11/2004 |
| WO | 2005067935 | A1 | 7/2005 |
| WO | 2006018182 | A1 | 2/2006 |
| WO | 2006018185 | A2 | 2/2006 |
| WO | 2006018220 | A2 | 2/2006 |
| WO | 2006018221 | A1 | 2/2006 |
| WO | 2006021378 | A1 | 3/2006 |
| WO | 2007090844 | A1 | 8/2007 |
| WO | 2009019205 | A1 | 2/2009 |

OTHER PUBLICATIONS

Turner, S., "The Design of Organic Syntheses". Elsevier, 1976, pp. 10 and 149.

Turner, W.W. et al., "Recent advances in the medicinal chemistry of antifungal agents". Current Pharmacutical Design, 1996, 2, pp. 209-224.

Verschuren, E.W. et al., "The cell cycle and how it is steered by Kaposi's sarcoma-associated herpesvirus cyclin". Journal of General Virology, 2004, 85, pp. 1347-1361.

Vippagunta, S. R. et al., "Crystalline solids". Advanced Drug Delivery Reviews, 48, 2001, pp. 3-26.

Visiting Nurse Association of America. www.vnaa.org/gen/Germ_Protection_Center_Cold_and_Flu_Resources,html, 2009.

Voskoglou-Nomikos, T. et al., "Clinical predictive value of the in vitro cell line, human xenograft, and mouse allograft preclinical cancer models". Clinical Cancer Research vol. 9, 2003, pp. 4227-4239.

Wagner, B. et al, "7-Benzylamino-6-chloro-2-piperazino-4-pyrrolidino-pteridine, a potent inhibitor of cAMP-specific phosphodiesterase, enhancing nuclear protein binding to the CRE consensus sequence in human tumour cells", Biochemical Pharmacology, Pergamon, Oxford, GB, 2002, pp. 659-668.

Wagner, G. et al., "Synthesis of new phrido[3',2':4,5] thieno '3,2-d] 1,2,3-triazine derivatives as antianaphylactics". Biosciences Dept of the University of Leipzig, Pharmazie (Pharmacy), 48, vol. 7,1993, pp. 514-518.

Webster's Comprehensive Dictionary, 1996, pp. 1013-1014.

Wikipedia. "Melting Point", Jan. 17, 2007. http://en.wikipedia.org/wiki/Melting_point.

Wolf, D. E.et al., "The structure of rhizopterin". Contribution from the Research Labs of Merck and Co. Inc. Nov. 1947, Journal of American Chem. Soc., vol. 69, pp. 2753- 2759. XP002352205.

ACPS Meeting, Background Information. "Scientific considerations of plymorphism in pharmaceutical solids: abbreviated new drug applications". Oct. 2002.

Ahlenius, T. List of cardiovascular disorder/diseases. Ahlenius, Karolinska Institutet. Stockholm, Sweden. Cardiovascular Diseases, p. 1-34, Apr. 2007.

Ahmad, N. "Polo-like kinase (Plk) 1: a novel target for the treatment of prostate cancer". The FASEB Journal. 2004, 18:5-7. Dept of Dermatology, Univ. Wisconsin, pp. 5-7.

Arnold, K. "Collaboration to play key role in NCI's future, director says". Journal of the National Cancer Institute, Jun. 5, 2002, pp. 790-792, vol. 94, No. 11.

BBC News/Health, Killer Breast Cancern Therapy Hope, www.newsvote.bbc/co./uk, Published Jan. 21, 2006.

Bennett, J.C., et al., "Textbook of Medicine", Part XIV, Oncology, 1997.

Blain, S. W. et al., "Differential interaction of the cyclin-dependent kinase (Cdk) Inhibitor p27KIP with cyclin A-Cdk2 and cyclin D2-Cdk4". The Journal of Biological Chemistry, vol. 272, No. 41, Issue Oct. 10, 1997, pp. 25862-25872.

Chen, J.X. et al., "Parallel differentiated recognition of ketones and acetals". Angewandte Chemie Int. Ed, vol. 37, Issue 1/2, p. 91-93, 1998.

Dipolar aprotic solvent. Exhibit A, IUPAC Compendium of Chemical Terminology, 2nd Edition, 1997.

Doerwald, F.Z. Book Wiley-VCH Verlag GmbH & Co. KGaA, "Side reactions in organice synthesis: A Guide to Successful Synthesis Design". 2005.

Eurasian Opinion, Appln No. 2007/00389/28, Maly Slatoustinsky per., d.10, kv.15, 101000 Moscow, Russia, "EVROMARKPAT", 2007.

Ferrand, G., et al., "Synthesis and potential antiallergic activity of new pteridinones and related compounds". Eur. J. Med. Chem, 31, 1996, pp. 273-280. XP--2246920.

Ghandi, L., et al., "An Open-Label Phase II Trial of the PLK Inhibitor BI 2536 in Patients with Sensitive Relapse Small Cell Lung Cancer". ASCO Meeting 2009.

Giron, G. "Thernal analysis and calorimetric methods in the characterization of plymorphs and solvates". Thermochimica Acta 248, 1995, pp. 1-59.

Goodman-Gilman's "The Pharmacological Basis of Therapeutics". Ninth edition, 1996, pp. 1225-1271.

International Search Report for PCT/EP03/01935 mailed Jul. 23, 2003.

Ito, Y., et al., "Polo-like kinase 1 (PLK) expression is associated with cell proliferative activity and cdc2 expression in malignant-lymphoma of the thyroid". Anticancer Research, 2004, vol. 24, No. 1, pp. 259-263.

Jamieson, C. et al., "Application of ReactArray Robotics and Design of Experiments Techniques in Optimisation of Supported Reagent Chemistry". Org. Proc. Res. & Dev., 2002, 6, p. 823-825.

Jaworska, J., et al., "Review of methods for assessing the applicability domains of SARS and QSARS". Sponsor: The European Commission—Joint Research Ctr., Institute for Health and Consumer Protection—ECVAM, Italy, 2004.

Kashima, M. K. et al., "Expression of polo-like kinase (PLK1) in non-Hodgkin's lymphomas". NCBI, PubMed, 2005.

Kimball, S. D. et al., "Cell cycle kinases and checkpoint regulation in cancer". Annual Reports in Medicinal Chemistry, 36, Chapter 14, 2001, pp. 139-148.

Leukemia & Lymphoma Society—Disease Information-Lymphoma. www.leukemia-lymphoma.org/all_page? item_id-7030, 2008.

Leukemia & Lymphoma Society—Disease Information. www.leukemia-lymphoma.org/all_page?item_id-7026, 2008.

Marko, D. et al., "Intracellular localization of 7-benzylamino-6-chloro-2-piperazino-4-pyrrolidino-pteridine in membrane structures impeding the inhibition of cytosolic cyclic AMP-specific phosphodiesterase". Biochemical Pharmacology, 63, 2002, pp. 669-676.

Masuda, Y. et al., "B-Hydroxyisovalerylshikonin induces apoptosis in human leukemia cells by inhibiting the activity of a polo-like kinase 1 (PLK)". 2003, Oncogene, 22, pp. 1012-1023.

Mayer, SF, et al., "Enzyme-initiated domino (cascase) reactions". Chem. Soc. Rev, 2001, p. 332-339.

MedlinePlus: Bacterial Infections. www.nim.nih.gov/medlineplus/print/bacterialinfections.htm, date last updated Mar. 25, 2009.

MedlinePlus: Viral Infections. www.nim.nih.gov/medlineplus/printiviralinfections.htm, date last updated Feb. 11, 2009.

Merck Manual of Medical Information—Home Edition, Section 17. "Parasitic Infections". Chapter 184, 2003.

Mito, K., et al., "Expression of polo-like kinase (PLK1) in non-Hodgkin's lymphomas". NCBI, PubMed, 2005, Leuk. Lymphoma, 46(2), pp. 251-231.

Nagao, K. et al., "Effect of MX-68 on airway inflammation and hyperresponsiveness in mice and guinea-pigs". Journal of Pharmacy and Pharmacology, JPP 2004, 56, pp. 187-196.

National Institute of Neurological Disorders, Index Stroke, 2006.

Norman, P. "PDE4 inhibitors". Ashley Publications Ltd., Expert Opinions Ther. Patents, 1999, pp. 1101-1118.

Office Action mailed Dec. 10, 2003 for U.S. Appl. No. 10/226,710, filed Aug. 23, 2002. (Boehringer Ingelheim Docket No. 01-1250).

Office Action mailed Apr. 28, 2004 for U.S. Appl. No. 10/374,876, filed Feb. 26, 2003 (Boehringer Ingelheim Docket No. 01-1462).

Ohio Dept of Health, "Brain and Other Central Nervous System Cancer in Ohio, 1997-2001". Sep. 2004, pp. 1-4.

Organic Chemistry, Grupo Editorial Iberoamerica, Section 13, 3, pp. 301-302, 1983 (best copy available in Spanish).

Rocha Lima, C.M. et al. "Randomized phase II trial of gemcitabine plus irinotecan or docetaxel uin stage IIIB or stage IV NSCLC" Annals of Oncology, 15(3), p. 410-418, 2004.

Rylander, P.N. "Hydrgenation Methods". 1985, Chapter 13.

Rylander, P.N. "Hydrgenation Methods". 1985, Chapters 3, 4.

Rylander, P.N. "Hydrgenation Methods". 1985, Chapters 8, 9, 10, 11.

Rylander, P.N. "Hydrgenation Methods". 1985, Chapter 5, 6, 7.

Rylander, P.N., "Hydrogenation Methods". 1985, Chapters 1, 2.

Santing, R. E. et al., "Brochodilatory and anti-inflammatory properties of inhaled selective phosphodiesterase inhibitors in a guinea model of allergic asthma" . European Journal of Pharmacology, 429, 2001, pp. 335-344.

Savelli, F. et al., "Heterotricyclic system Part II—synthesis of new pyrido[1'2':4,5]pyrazino[3,2-d] pyrimidines". Bollettino Chimico Farmaceutico, 131(8), Sep. 1992, pp. 309-312.

Science, vol. 310, Oct. 21, 2005, p. 409, Chemistry: One After Another.

Snyder, J. S. et al., "Common bacteria whose susceptibility to antimicrobials is no longer predictable". NCBI, PubMed, 2000, Le Journal Medical Libanais (The Lebanse Medical Journal), 48, pp. 208-214.

Souillac, P. et al., "Characterization of delivery systems, differential scanning calorimetry". (in Encyclopedia of Controlled Drug Delivery), 1999, John Wiley & Sons, pp. 212-227.

Sugar, A. M. et al., "Comparison of three methods of antifungal susceptibility testing with the proposed NCCLS standard broth macrodilution assay: lack of effect of phenol red". Mycology, Diagn Microbiol. Infect. Dis. 1995, 21- pp. 129-133.

Takai, N. et al., "Polo-like kinases (PLKs) and cancer". Oncogene , 2005, 24, pp. 287-291.

Dyson, G, et al. "The Chemistry of Synthetic Drugs". 1964, p. 12-19.

Mashkovkii, M.D., "Medicaments". Moscow, Novaja Volna, 2001, vol. 1, p. 11.

Mashkovskii, M.D. "Drugs", Handbook for Doctors, 1993, Part I, Ch.1, p. 8.

McInnes, C. "Inhibitors of polo-like kinase reveal roles in spindle-pole maintenance". Nature Chemical Biology, vol. 2, No. 11, Nov. 2006, p. 608.

Mikhailov, I.B., Principles of Rational Pharmacotherapy. Handbook for clinical pharmacology for students of pediatric and medical faculties of medical high schools, St. Petersburg, Russia, "Foliant", 1999, p. 25.

Neidle, S. ed., "Cancer Drug Design and Discovery", Elsevier/Academic Press, 2008, p. 427-431.

Steegmaier, M. et al. "BI 2536, a potent and selective inhibitor of polo-like kinase 1, inhibits tumor growth in vivo". Current Biology, 2007, 17(4), p. 316-322.

Stephenson, D.T. et al. "The effects of a selective dopamine D2 receptor agonist on behavioral and pathological outcome in 1-methl-4-phenyl-1,2,3,6-tetrahydropyridine-treated squirrel monkeys". J. Pharmacology and Experimental Therapeutics, vol. 303, No. 2, 2002, p. 1257.

Walsh, F. "No "Magic Bullet" Cure for Cancer". BBC News Feb. 1, 2007, http://news.bbc,co.uk/2/health/6310697.stm, downloaded Jul. 6, 2010.

* cited by examiner

DIHYDROPTERIDINONE COMPOUNDS

RELATED APPLICATION DATA

This application is a continuation application of U.S. application Ser. No. 11/219,728 filed May 30, 2008, which is a divisional of U.S. Pat. No. 7,786,299 filed Sep. 6, 2005, which is a continuation of U.S. application Ser. No. 10/903,807 filed Jul. 30, 2004, which is a continuation of U.S. Pat. No. 6,681,422 filed Feb. 26, 2003.

The present invention relates to new dihydropteridinones of general formula (I)

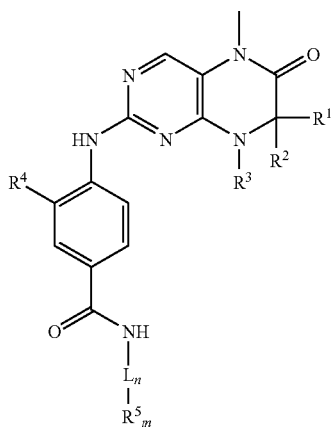

(I)

wherein the groups L, $R^1$, $R^2$, $R^3$, $R^4$ and $R^5$ have the meanings given in the claims and specification, the isomers thereof, processes for preparing these dihydropteridinones and the use thereof as pharmaceutical compositions.

BACKGROUND TO THE INVENTION

Pteridinone derivatives are known from the prior art as active substances with an antiproliferative activity. WO 01/019825 describes the use of pteridinone derivatives for the treatment of neoplastic and viral diseases. The resistance of many types of tumours calls for the development of new pharmaceutical compositions for combating tumours.

The aim of the present invention is to prepare new compounds with antiinflammatory and antiproliferative activity.

DETAILED DESCRIPTION OF THE INVENTION

Surprisingly it has been found that compounds of general formula (I) wherein the groups L and $R^1$ to $R^5$ have the meanings given hereinafter act as inhibitors of specific cell cycle kinases. Thus, the compounds according to the invention may be used for example to treat diseases connected with the activity of specific cell cycle kinases and characterised by excessive or abnormal cell proliferation.

The present invention therefore relates to compounds of general formula (I)

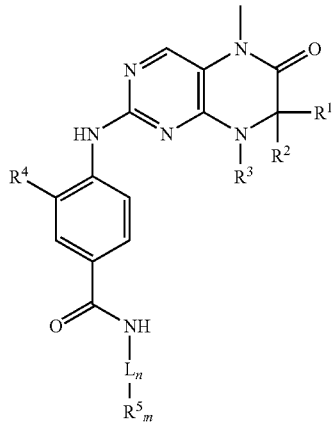

(I)

wherein
$R^1$, $R^2$ which may be identical or different, denote hydrogen or optionally substituted $C_1$-$C_6$-alkyl, or
$R^1$ and $R^2$ together denote a 2- to 5-membered alkyl bridge which may contain 1 to 2 heteroatoms,
$R^3$ denotes hydrogen or a group selected from among optionally substituted $C_1$-$C_{12}$-alkyl, $C_2$-$C_{12}$-alkenyl, $C_2$-$C_{12}$-alkynyl and $C_6$-$C_{14}$-aryl, or
a group selected from among optionally substituted and/or bridged $C_3$-$C_{12}$-cycloalkyl, $C_3$-$C_{12}$-cycloalkenyl, $C_7$-$C_{12}$-polycycloalkyl, $C_7$-$C_{12}$-polycycloalkenyl, $C_5$-$C_{12}$-spirocycloalkyl, $C_3$-$C_{12}$-heterocycloalkyl which contains 1 to 2 heteroatoms, and $C_3$-$C_{12}$-heterocycloalkenyl which contains 1 to 2 heteroatoms, or
$R^1$ and $R^3$ or $R^2$ and $R^3$ together denote a saturated or unsaturated $C_3$-$C_4$-alkyl bridge which may contain 1 heteroatom,
$R^4$ denotes a group selected from among hydrogen, —CN, hydroxy, —$NR_6R_7$ and halogen, or
a group selected from among optionally substituted $C_1$-$C_6$-alkyl, $C_2$-$C_6$-alkenyl, $C_2$-$C_6$-alkynyl, $C_1$-$C_5$-alkyloxy, $C_2$-$C_5$-alkenyloxy, $C_2$-$C_5$-alkynyloxy, $C_1$-$C_6$-alkylthio, $C_1$-$C_6$-alkylsulphoxo and $C_1$-$C_6$-alkylsulphonyl,
L denotes a linker selected from among optionally substituted $C_2$-$C_{10}$-alkyl, $C_2$-$C_{10}$-alkenyl, $C_6$-$C_{14}$-aryl, —$C_2$-$C_4$-alkyl-$C_6$-$C_{14}$-aryl, —$C_6$-$C_{14}$-aryl-$C_1$-$C_4$-alkyl, optionally bridged $C_3$-$C_{12}$-cycloalkyl and heteroaryl which contains 1 or 2 nitrogen atoms,
n denotes 0 or 1
m denotes 1 or 2
$R^5$ denotes a group selected from among optionally substituted morpholinyl, piperidinyl, piperazinyl, piperazinylcarbonyl, pyrrolidinyl, tropenyl, $R^8$-diketomethylpiperazinyl, sulphoxomorpholinyl, sulphonylmorpholinyl, thiomorpholinyl, —$NR^8R^9$ and azacycloheptyl,
$R^6$, $R^7$ which may be identical or different, denote hydrogen or $C_1$-$C_4$-alkyl, and
$R^8$, $R^9$ denote unsubstituted nitrogen substituents at $R^5$, which may be identical or different, denote either hydrogen or a group selected from among $C_1$-$C_6$-alkyl, —$C_1$-$C_4$-alkyl-$C_3$-$C_{10}$-cycloalkyl, $C_3$-$C_{10}$-cycloalkyl, $C_6$-$C_{14}$-aryl, —$C_1$-$C_4$-alkyl-$C_6$-$C_{14}$-aryl, pyranyl, pyridinyl, pyrimidinyl, $C_1$-$C_4$-alkyloxycarbonyl, $C_6$-$C_{14}$-arylcarbonyl, $C_1$-$C_4$-alkylcarbonyl, $C_6$-$C_{14}$-arylmethyloxycarbonyl, $C_6$-$C_{14}$-arylsulphonyl, $C_1$-$C_4$-alkylsulphonyl- and $C_6$-$C_{14}$-aryl-$C_1$-$C_4$-alkylsulphonyl-, optionally in the form of the tautomers, the racemates, the enantiomers, the diastereomers and the mixtures thereof, and optionally the pharmacologically acceptable acid addition salts thereof.

Preferred compounds of formula (I) are those wherein
$R^1$ to $R^4$, $R^6$ and $R^7$ are as hereinbefore defined, and
L denotes a linker selected from among optionally substituted $C_2$-$C_{10}$-alkyl, $C_2$-$C_{10}$-alkenyl, $C_6$-$C_{14}$-aryl, —$C_2$-$C_4$-alkyl-$C_6$-$C_{14}$-aryl, —$C_6$-$C_{14}$-aryl-$C_1$-$C_4$-alkyl, optionally bridged $C_3$-$C_{12}$-cycloalkyl and heteroaryl which contains 1 or 2 nitrogen atoms
n denotes 1
m denotes 1 or 2
$R^5$ denotes a group which is bound to L via a nitrogen atom, selected from among optionally substituted morpholinyl, piperidinyl, $R^8$-piperazinyl, pyrrolidinyl, tropenyl, $R^8$-diketomethylpiperazinyl, sulphoxomorpholinyl, sulphonylmorpholinyl, thiomorpholinyl, —$NR^8R^9$ and azacycloheptyl,
$R^8$, $R^9$ denote unsubstituted nitrogen substituents at $R^5$, which may be identical or different, hydrogen or a group selected from among $C_1$-$C_6$-alkyl, —$C_1$-$C_4$-alkyl-$C_3$-$C_{10}$-cycloalkyl, $C_3$-$C_{10}$-cycloalkyl, $C_6$-$C_{14}$-aryl, —$C_1$-$C_4$-alkyl-$C_6$-$C_{14}$-aryl, pyranyl, pyridinyl, pyrimidinyl, $C_1$-$C_4$-alkyloxycarbonyl, $C_6$-$C_{14}$-arylcarbonyl, $C_1$-$C_4$-alkylcarbonyl, $C_6$-$C_{14}$-arylmethyloxycarbonyl, $C_6$-$C_{14}$-arylsulphonyl, $C_1$-$C_4$-alkylsulphonyl and $C_6$-$C_{14}$-aryl-$C_1$-$C_4$-alkylsulphonyl,
optionally in the form of the tautomers, the racemates, the enantiomers, the diastereomers and the mixtures thereof, and optionally the pharmacologically acceptable acid addition salts thereof.

Also preferred are compounds of formula (I), wherein
$R^1$ to $R^4$, $R^6$ and $R^7$ are as hereinbefore defined,
L denotes a linker selected from among optionally substituted $C_2$-$C_{10}$-alkyl, $C_2$-$C_{10}$-alkenyl, $C_6$-$C_{14}$-aryl, —$C_2$-$C_4$-alkyl-$C_6$-$C_{14}$-aryl, —$C_6$-$C_{14}$-aryl-$C_1$-$C_4$-alkyl, optionally bridged $C_3$-$C_{12}$-cycloalkyl and heteroaryl which contains 1 or 2 nitrogen atoms
n denotes 0 or 1
m denotes 1 or 2
$R^5$ denotes a group which is bound to L via a carbon atom, selected from among $R^8$-piperidinyl, $R^8R^9$-piperazinyl, $R^8$-pyrrolidinyl, $R^8$-piperazinylcarbonyl, $R^8$-tropenyl, $R^8$-morpholinyl and $R^8$-azacycloheptyl, and
$R^8$, $R^9$ denote unsubstituted nitrogen substituents at $R^5$, which may be identical or different, hydrogen or a group selected from among $C_1$-$C_6$-alkyl, —$C_1$-$C_4$-alkyl-$C_3$-$C_{10}$-cycloalkyl, $C_3$-$C_{10}$-cycloalkyl, $C_6$-$C_{14}$-aryl, —$C_1$-$C_4$-alkyl-$C_6$-$C_{14}$-aryl, pyranyl, pyridinyl, pyrimidinyl, $C_1$-$C_4$-alkyloxycarbonyl, $C_6$-$C_{14}$-arylcarbonyl, $C_1$-$C_4$-alkylcarbonyl, $C_6$-$C_{14}$-arylmethyloxycarbonyl, $C_6$-$C_{14}$-arylsulphonyl, $C_1$-$C_4$-alkylsulphonyl and $C_6$-$C_{14}$-aryl-$C_1$-$C_4$-alkylsulphonyl,
optionally in the form of the tautomers, the racemates, the enantiomers, the diastereomers and the mixtures thereof, and optionally the pharmacologically acceptable acid addition salts thereof.

Particularly preferred are compounds of formula I wherein L, m, n and $R^3$ to $R^9$ are as hereinbefore defined, and
$R^1$, $R^2$ which may be identical or different, denote a group selected from among hydrogen, Me, Et, Pr, or
$R^1$ and $R^2$ together form a $C_2$-$C_4$-alkyl bridge,
optionally in the form of the tautomers, the racemates, the enantiomers, the diastereomers and the mixtures thereof, and optionally the pharmacologically acceptable acid addition salts thereof.

Especially preferred are compounds of formula I wherein $R^1$, $R^2$, m, n and $R^5$ to $R^8$ are as hereinbefore defined, and
$R^3$ denotes a group selected from among optionally substituted $C_1$-$C_{10}$-alkyl, $C_3$-$C_7$-cycloalkyl, $C_3$-$C_6$-heterocycloalkyl and $C_6$-$C_{14}$-aryl or
$R^1$ and $R^3$ or $R^2$ and $R^3$ together denote a saturated or unsaturated $C_3$-$C_4$-alkyl bridge which may contain 1 to 2 heteroatoms,
$R^4$ denotes a group selected from among hydrogen, OMe, OH, Me, Et, Pr, OEt, NHMe, $NH_2$, F, CL, Br, O-propargyl, O-butynyl, CN, SMe, $NMe_2$, $CONH_2$, ethynyl, propynyl, butynyl and allyl, and
L denotes a linker selected from among optionally substituted phenyl, phenylmethyl, cyclohexyl and branched $C_1$-$C_6$-alkyl,
optionally in the form of the tautomers, the racemates, the enantiomers, the diastereomers and the mixtures thereof, and optionally the pharmacologically acceptable acid addition salts thereof.

The invention further relates to compounds of formula I for use as pharmaceutical compositions.

Of particular importance according to the invention are compounds of formula I for use as pharmaceutical compositions with an antiproliferative activity.

The invention also relates to the use of a compound of formula I for preparing a pharmaceutical composition for the treatment and/or prevention of cancer, infections, inflammatory and autoimmune diseases.

The invention also relates to a method of treating and/or preventing cancer, infections, inflammatory and autoimmune diseases, characterised in that a patient is given an effective amount of a compound of formula I.

The invention also relates to pharmaceutical preparations, containing as active substance one or more compounds of general formula (I) or the physiologically acceptable salts thereof, optionally combined with conventional excipients and/or carriers.

The invention also relates to a process for preparing a compound of general formula (I),

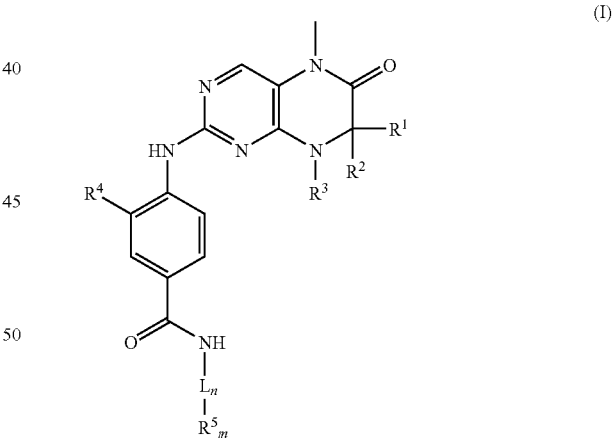

wherein
$R^1$-$R^5$, m, n and L are as hereinbefore defined,
characterised in that a compound of general formula (II)

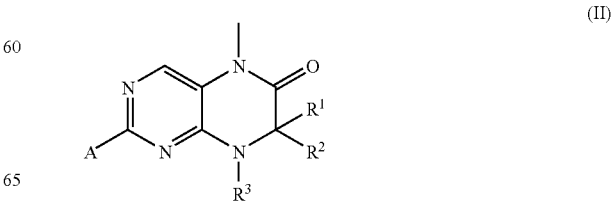

wherein
R¹-R³ are as hereinbefore defined and A is a leaving group, is reacted with an optionally substituted compound of general formula (III),

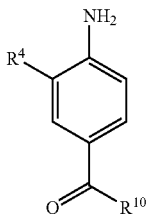

(III)

wherein
R⁴ is as hereinbefore defined and
R¹⁰ denotes OH, NH-L-R⁵, —O-methyl, —O-ethyl,
and optionally then the product of general formula (IV)

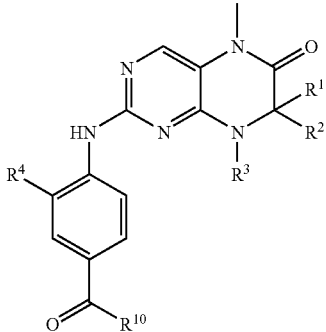

(IV)

wherein
R¹ to R⁴ is as hereinbefore defined and
R¹⁰ denotes OH, —NH-L-R⁵, —O-methyl or —O-ethyl,
optionally after previous hydrolysis of the ester group —COR¹⁰, is reacted with an amine of general formula (V)

NH₂-L-R⁵ₘ    (V)

wherein
R⁵ is as hereinbefore defined.

The invention further relates to a compound of formula (II),

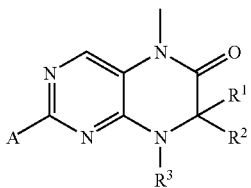

(II)

wherein
R¹-R³ are as hereinbefore defined and A is a leaving group.

The term alkyl groups, including alkyl groups which are a part of other groups, denotes branched and unbranched alkyl groups with 1 to 12 carbon atoms, preferably 1-6, most preferably 1-4 carbon atoms, such as, for example: methyl, ethyl, propyl, butyl, pentyl, hexyl, heptyl, octyl, nonyl, decyl and dodecyl. Unless otherwise stated, the abovementioned terms propyl, butyl, pentyl, hexyl, heptyl, octyl, nonyl, decyl and dodecyl include all the possible isomeric forms. For example, the term propyl includes the two isomeric groups n-propyl and iso-propyl, the term butyl includes n-butyl, iso-butyl, sec. butyl and tert.-butyl, the term pentyl includes iso-pentyl, neo-pentyl, etc.

In the abovementioned alkyl groups one or more hydrogen atoms may optionally be replaced by other groups. For example these alkyl groups may be substituted by fluorine. All the hydrogen atoms of the alkyl group may optionally also be replaced.

The term alkyl bridge, unless otherwise stated, denotes branched and unbranched alkyl groups with 1 to 5 carbon atoms, for example methylene, ethylene, propylene, isopropylene, n-butylene, iso-butyl, sec. butyl and tert.-butyl etc. bridges. Methylene, ethylene, propylene and butylene bridges are particularly preferred. In the alkyl bridges mentioned 1 to 2 C-atoms may optionally be replaced by one or more heteroatoms selected from among oxygen, nitrogen or sulphur.

The term alkenyl groups (including those which are a part of other groups) denotes branched and unbranched alkylene groups with 2 to 10 carbon atoms, preferably 2-6 carbon atoms, most preferably 2-3 carbon atoms, provided that they have at least one double bond. Examples include: ethenyl, propenyl, butenyl, pentenyl etc. Unless otherwise stated, the abovementioned terms propenyl, butenyl, etc also include all the possible isomeric forms. For example, the term butenyl includes 1-butenyl, 2-butenyl, 3-butenyl, 1-methyl-1-propenyl, 1-methyl-2-propenyl, 2-methyl-1-propenyl, 2-methyl-2-propenyl and 1-ethyl-1-ethenyl.

In the abovementioned alkenyl groups, unless otherwise stated, one or more hydrogen atoms may optionally be replaced by other groups. For example, these alkyl groups may be substituted by the halogen atom fluorine. All the hydrogen atoms of the alkenyl group may optionally also be replaced.

The term alkynyl groups (including those which are a part of other groups) denotes branched and unbranched alkynyl groups with 2 to 10 carbon atoms, provided that they have at least one triple bond, for example ethynyl, propargyl, butynyl, pentynyl, hexynyl etc., preferably ethynyl or propynyl.

In the abovementioned alkynyl groups, unless otherwise stated, one or more hydrogen atoms may optionally be replaced by other groups. For example, these alkyl groups may be substituted by fluorine. All the hydrogen atoms of the alkynyl group may optionally also be replaced.

The term aryl denotes an aromatic ring system with 6 to 14 carbon atoms, preferably 6 or 10 carbon atoms, preferably phenyl, which, unless otherwise stated, may carry one or more of the following substituents, for example: OH, NO₂, CN, OMe, —OCHF₂, —OCF₃, —NH₂, halogen, for example fluorine or chlorine, $C_1$-$C_{10}$-alkyl, preferably $C_1$-$C_5$-alkyl, preferably $C_1$-$C_3$-alkyl, most preferably methyl or ethyl, —O—$C_1$-$C_3$-alkyl, preferably —O-methyl or —O-ethyl, —COOH, —COO—$C_1$-$C_4$-alkyl, preferably —O-methyl or —O-ethyl, —CONH₂.

Examples of heteroaryl groups wherein up to two carbon atoms are replaced by one or two nitrogen atoms include pyrrole, pyrazole, imidazole, triazole, pyridine, pyrimidine, while each of the abovementioned heteroaryl rings may optionally also be anellated to a benzene ring, preferably benzimidazole, and unless otherwise stated these heterocycles may carry one or more of the following substituents, for example: F, Cl, Br, OH, OMe, methyl, ethyl, CN, CONH₂, NH₂, optionally substituted phenyl, optionally substituted heteroaryl, preferably optionally substituted pyridyl.

Examples of cycloalkyl groups are cycloalkyl groups with 3-12 carbon atoms, for example cyclopropyl, cyclobutyl, cyclopentyl, cyclohexyl, cycloheptyl or cyclooctyl, preferably cyclopropyl, cyclopentyl or cyclohexyl, while each of the abovementioned cycloalkyl groups may optionally also carry one or more substituents, for example: OH, $NO_2$, CN, OMe, $-OCHF_2$, $-OCF_3$, $-NH_2$ or halogen, preferably fluorine or chlorine, $C_1$-$C_{10}$-alkyl, preferably $C_1$-$C_5$-alkyl, preferably $C_1$-$C_3$-alkyl, more preferably methyl or ethyl, $-O-C_1$-$C_3$-alkyl, preferably $-O$-methyl or $-O$-ethyl, $-COON$, $-COO-C_1$-$C_4$-alkyl, preferably $-COO$-methyl or $-COO$-ethyl or $-CONH_2$. Particularly preferred substituents of the cycloalkyl groups are $=O$, OH, $NH_2$, methyl or F.

Examples of cycloalkenyl groups are cycloalkyl groups with 3-12 carbon atoms which have at least one double bond, for example cyclopropenyl, cyclobutenyl, cyclopentenyl, cyclohexenyl or cycloheptenyl, preferably cyclopropenyl, cyclopentenyl or cyclohexenyl, while each of the abovementioned cycloalkenyl groups may optionally also carry one or more substituents.

"$=O$" denotes an oxygen atom linked via a double bond.

Examples of heterocycloalkyl groups, unless otherwise described in the definitions, include 3- to 12-membered, preferably 5-, 6- or 7-membered, saturated or unsaturated heterocycles which may contain as heteroatoms nitrogen, oxygen or sulphur, for example tetrahydrofuran, tetrahydrofuranone, γ-butyrolactone, α-pyran, γ-pyran, dioxolane, tetrahydropyran, dioxane, dihydrothiophene, thiolan, dithiolan, pyrroline, pyrrolidine, pyrazoline, pyrazolidine, imidazoline, imidazolidine, tetrazole, piperidine, pyridazine, pyrimidine, pyrazine, piperazine, triazine, tetrazine, morpholine, thiomorpholine, diazepan, oxazine, tetrahydro-oxazinyl, isothiazole, pyrazolidine, preferably morpholine, pyrrolidine, piperidine or piperazine, while the heterocyclic group may optionally carry substituents, for example $C_1$-$C_4$-alkyl, preferably methyl, ethyl or propyl.

Examples of polycycloalkyl groups are optionally substituted, bi-, tri-, tetra- or pentacyclic cycloalkyl groups, for example pinane, 2,2,2-octane, 2,2,1-heptane or adamantane. Examples of polycycloalkenyl groups are optionally bridged and/or substituted 8-membered bi-, tri-, tetra- or pentacyclic cycloalkenyl groups, preferably bicycloalkenyl or tricycloalkenyl groups, if they have at least one double bond, for example norbornene.

Examples of spiroalkyl groups are optionally substituted spirocyclic $C_5$-$C_{12}$ alkyl groups.

Generally, the term halogen denotes fluorine, chlorine, bromine or iodine, preferably fluorine, chlorine or bromine, most preferably chlorine.

The leaving group A denotes either identical or different leaving groups such as for example -o-methyl, —SCN, chlorine, bromine, iodine, methanesulphonyl, trifluoromethanesulphonyl or p-toluenesulphonyl, preferably chlorine.

The compounds according to the invention may be present in the form of the individual optical isomers, mixtures of the individual enantiomers, diastereomers or racemates, in the form of the tautomers and also in the form of the free bases or the corresponding acid addition salts with pharmacologically acceptable acids—such as for example acid addition salts with hydrohalic acids, for example hydrochloric or hydrobromic acid, or organic acids, such as for example oxalic, fumaric, diglycolic or methanesulphonic acid.

The substituent $R^1$ may denote hydrogen or a group selected from among optionally substituted and/or branched $C_1$-$C_6$-alkyl, preferably methyl or ethyl, more preferably methyl or ethyl.

The substituent $R^2$ may denote hydrogen or a group selected from among optionally substituted and/or branched $C_1$-$C_6$-alkyl, preferably methyl or ethyl.

$R^1$ and $R^2$ together may denote a 2- to 5-membered alkyl bridge, preferably an ethylene, propylene or butylene bridge which may contain 1 to 2 heteroatoms, preferably oxygen or nitrogen, more preferably ethylene, propylene.

The substituent $R^3$ may denote hydrogen or a group selected from among optionally substituted and/or branched $C_1$-$C_{12}$-alkyl, preferably ethyl, propyl, butyl, pentyl or hexyl, more preferably propyl, butyl, pentyl or hexyl, $C_2$-$C_{12}$-alkenyl, preferably $C_5$-$C_7$-alkenyl, $C_2$-$C_{12}$-alkynyl, preferably $C_5$-$C_7$-alkynyl and $C_6$-$C_{14}$-aryl, preferably phenyl, a group selected from among optionally substituted and/or bridged $C_3$-$C_{12}$-cycloalkyl, preferably cyclopentyl or cyclohexyl, $C_3$-$C_{12}$-cycloalkenyl, preferably $C_6$-$C_7$-cycloalkenyl, $C_7$-$C_{12}$-polycycloalkyl, $C_7$-$C_{12}$-polycycloalkenyl, $C_6$-$C_{12}$-spirocycloalkyl, $C_3$-$C_{12}$-heterocycloalkyl, preferably pyranyl or piperinyl, pyrrolidinyl, pyrazinyl or morpholinyl which contains 1 to 2 heteroatoms, preferably oxygen or nitrogen, and $C_3$-$C_{12}$-heterocycloalkenyl which contains 1 to 2 heteroatoms, preferably oxygen or nitrogen.

Most preferably, the substituent $R^3$ denotes isopropyl, isobutyl, isopentyl, cyclopentyl, phenyl or cyclohexyl.

$R^1$ and $R^3$ or $R^2$ and $R^3$ together may denote a saturated or unsaturated $C_3$-$C_4$-alkyl bridge which may contain 1 heteroatom, preferably oxygen or nitrogen.

The substituent $R^4$ may denote a group selected from among hydrogen, —CN, hydroxy, —$NR^6R^7$ and Halogen, preferably chlorine or fluorine, more preferably chlorine or a group selected from among optionally substituted $C_1$-$C_6$-alkyl, preferably methyl, ethyl or propyl, $C_2$-$C_6$-alkenyl, preferably ethenyl or propenyl, $C_2$-$C_6$-alkynyl, preferably ethynyl, propynyl or butynyl, $C_1$-$C_5$-alkyloxy, preferably methoxy, ethoxy or propargyloxy, $C_2$-$C_5$-alkenyloxy, $C_2$-$C_5$-alkynyloxy, $C_1$-$C_6$-alkylthio, $C_1$-$C_6$-alkylsulphoxo and $C_1$-$C_6$-alkylsulphonyl.

Most preferably, the substituent $R^4$ denotes methoxy, methyl, ethoxy, ethyl, propargyloxy or chlorine.

L may denote a linker selected from among optionally substituted $C_2$-$C_{10}$-alkyl, preferably ethyl, propyl, butyl or pentyl, $C_2$-$C_{10}$-alkenyl, $C_6$-$C_{14}$-aryl, preferably phenyl, —$C_2$-$C_4$-alkyl-$C_6$-$C_{14}$-aryl, —$C_6$-$C_{14}$-aryl-$C_1$-$C_4$-alkyl, preferably—phenyl-methyl, optionally bridged $C_3$-$C_{12}$-cycloalkyl, preferably cyclohexyl, and heteroaryl which contains 1 or 2 nitrogen atoms.

n denotes 0 or 1 m denotes 1 or 2, preferably 1.

$R^5$ may denote a group selected from among optionally substituted morpholinyl, piperidinyl, piperazinyl, piperazinylcarbonyl, pyrrolidinyl, tropenyl, $R^8$-diketomethylpiperazinyl, sulphoxomorpholinyl, sulphonylmorpholinyl, thiomorpholinyl, —$NR^8R^9$ and azacycloheptyl, preferably piperidinyl, morpholinyl, pyrrolidinyl, sulphoxomorpholiny, piperazinyl, thiomorpholinyl or tropenyl.

The groups $R^6$ and $R^7$ may be identical or different and may denote hydrogen or $C_1$-$C_4$-alkyl, preferably methyl or ethyl.

The groups $R^8$ and $R^9$ may be unsubstituted nitrogen substituents at $R^5$, they may be identical or different and denote either hydrogen or a group selected from among $C_1$-$C_6$-alkyl, preferably methyl, ethyl or propyl, —$C_1$-$C_4$-alkyl-$C_3$-$C_{10}$-cycloalkyl, preferably —$CH_2$-cyclopropyl, $C_3$-$C_{10}$-cycloalkyl, $C_6$-$C_{14}$-aryl, preferably phenyl, —$C_1$-$C_4$-alkyl-$C_6$-$C_{14}$-aryl, preferably benzyl, pyranyl, pyridinyl, pyrimidinyl, pyranyl, $C_1$-$C_4$-alkyloxycarbonyl, $C_6$-$C_{14}$-arylcarbonyl, $C_1$-$C_4$-alkylcarbonyl, $C_6$-$C_{14}$-arylmethyloxycarbonyl, $C_6$-$C_{14}$-arylsulphonyl, $C_1$-$C_4$-alkylsulphonyl and $C_6$-$C_{14}$-aryl-$C_1$-$C_4$-alkylsulphonyl.

Most preferably, the substituent $R^8$ denotes methyl, ethyl or propyl.

Most preferably, the substituent $R^9$ denotes methyl, ethyl or propyl.

$R^{10}$ may be a substituent selected from among OH, $NH_2$-LR5, —O-methyl and —O-ethyl, preferably OH, LR5, —O-methyl or —O-ethyl.

All the groups mentioned in the definition of $R^1$ to $R^{10}$ may optionally be branched and/or substituted.

The compounds according to the invention may be prepared by synthesis methods A described hereinafter, while the substituents of general formulae (A1) to (A9) have the meanings given hereinbefore. This method is to be understood as an illustration of the invention without restricting it to the subject matter thereof.

Method A

Step 1A

A compound of formula (A1) is reacted with a compound of formula (A2) to obtain a compound of formula (A3) (Diagram 1A). This reaction may be carried out according to WO 0043369 or WO 0043372. Compound (A1) is commercially obtainable, for example, from City Chemical LLC, 139 Allings Crossing Road, West Haven, Conn., 06516, USA. Compound (A2) may be prepared by procedures known from the literature: (a) F. Effenberger, U. Burkhart, J. Willfahrt *Liebigs Ann. Chem.* 1986, 314-333; b) T. Fukuyama, C.-K. Jow, M. Cheung, *Tetrahedron Lett.* 1995, 36, 6373-6374; c) R. K. Olsen, *J. Org. Chem.* 1970, 35, 1912-1915; d) F. E. Dutton, B. H. Byung *Tetrahedron Lett.* 1998, 30, 5313-5316; e) J. M. Ranajuhi, M. M. Joullie *Synth. Commun.* 1996, 26, 1379-1384.).

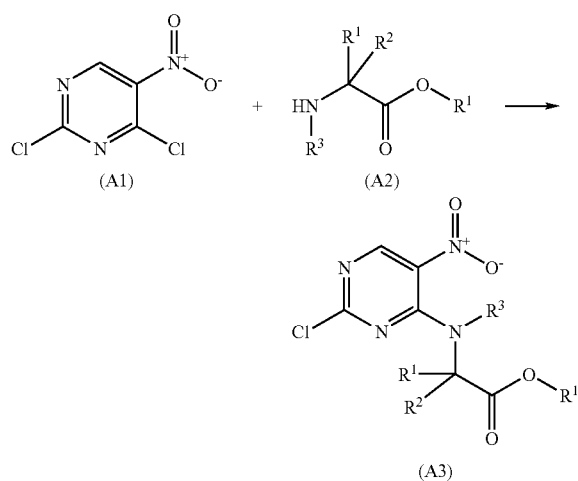

Diagram 1A

In Step 1A, 1 equivalent of the compound (A1) and 1 to 1.5 equivalents, preferably 1.1 equivalents of a base, preferably potassium carbonate, potassium hydrogen carbonate, sodium carbonate or sodium hydrogen carbonate, calcium carbonate, most preferably potassium carbonate, are stirred in a diluent optionally mixed with water, for example acetone, tetrahydrofuran, diethylether, cyclohexane, petroleum ether or dioxane, preferably cyclohexane or diethylether. At a temperature of 0 to 15° C., preferably 5 to 10° C., 1 equivalent of an amino acid of formula (A2), dissolved in an organic solvent, for example acetone, tetrahydrofuran, diethylether, cyclohexane or dioxane, is added dropwise. The reaction mixture is heated to a temperature of 18° C. to 30° C., preferably about 22° C., with stirring and then stirred for a further 10 to 24 hours, preferably about 12 hours. Then the diluent is distilled off, the residue is combined with water and the mixture is extracted two to three times with an organic solvent, such as diethylether or ethyl acetate, preferably ethyl acetate. The combined organic extracts are dried and the solvent is distilled off. The residue (compound A3) may be used in Step 2 without any prior purification.

Step 2A

The compound obtained in Step 1A (A3) is reduced at the nitro group and cyclised to form the compound of formula (A4) (Diagram 2A).

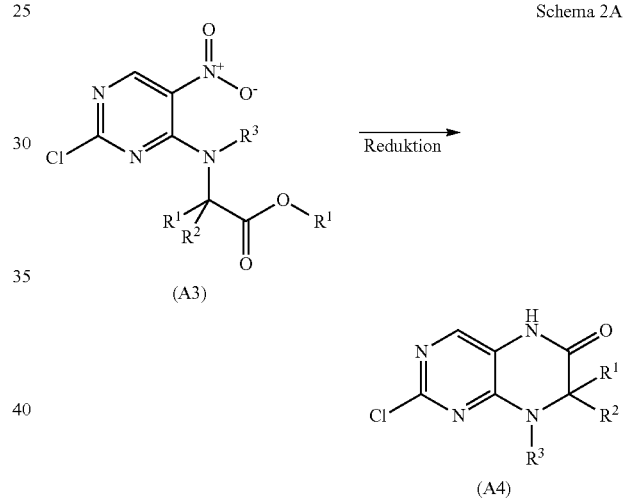

Diagram 2A

[Reduktion=reduction]

In Step 2A, 1 equivalent of the nitro compound (A3) is dissolved in an acid, preferably glacial acetic acid, formic acid or hydrochloric acid, preferably glacial acetic acid, and heated to 50 to 70° C., preferably about 60° C. Then a reducing agent, for example zinc, tin or iron, preferably iron filings, is added to complete the exothermic reaction and the mixture is stirred for 0.2 to 2 hours, preferably 0.5 hours, at 100 to 125° C., preferably at about 117° C. After cooling to ambient temperature the iron salt is filtered off and the solvent is distilled off. The residue is taken up in a solvent or mixture of solvents, for example ethyl acetate or dichloromethane/methanol 9/1 and semisaturated NaCl solution, and filtered through kieselgur, for example. The organic phase is dried and evaporated down. The residue (compound (A4)) may be purified by chromatography or by crystallisation or used as the crude product in Step 3A of the synthesis.

Step 3A

The compound obtained in Step 2A (A4) may be reacted by electrophilic substitution as shown in Diagram 3A to obtain the compound of formula (A5).

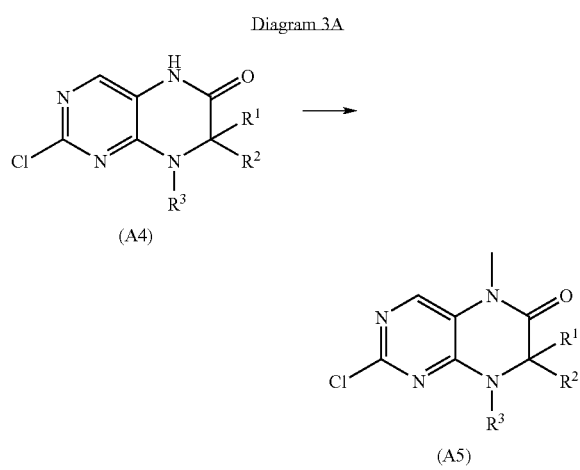

(A4)

(A5)

In Step 3A 1 equivalent of the amide of formula (A4) is dissolved in an organic solvent, for example dimethylformamide or dimethylacetamide, preferably dimethylacetamide, and cooled to about −5 to 5° C., preferably 0° C.

Then 0.9 to 1.3 equivalents of sodium hydride and 0.9 to 1.3 equivalents of a methylating reagent, e.g. methyl iodide, are added. The reaction mixture is stirred for 0.1-3 hours, preferably about 1 hour, at about 0 to 10° C., preferably at about 5° C., and may optionally be left to stand for a further 12 hours at this temperature. The reaction mixture is poured onto ice water and the precipitate is isolated. The residue (compound (A5)) may be purified by chromatography, preferably over silica gel, or by crystallisation, or used as the crude product in step 4A of the synthesis.

Step 4A

The amination of the compound (A5) obtained in Step 3A to yield the compound of formula (A9) (Diagram 4A) may be carried out using the methods known from the literature of variants 4.1 A (a) M. P. V. Boarland, J. F. W. McOmie *J. Chem. Soc.* 1951, 1218-1221; b) F. H. S. Curd, F. C. Rose *J. Chem. Soc.* 1946, 343-348., 4.2 A (a) Banks *J. Am. Chem. Soc.* 1944, 66, 1131 b) Ghosh and Dolly *J. Indian Chem. Soc.* 1981, 58, 512-513; c) N. P. Reddy and M. Tanaka *Tetrahedron Lett.* 1997, 38, 4807-4810.

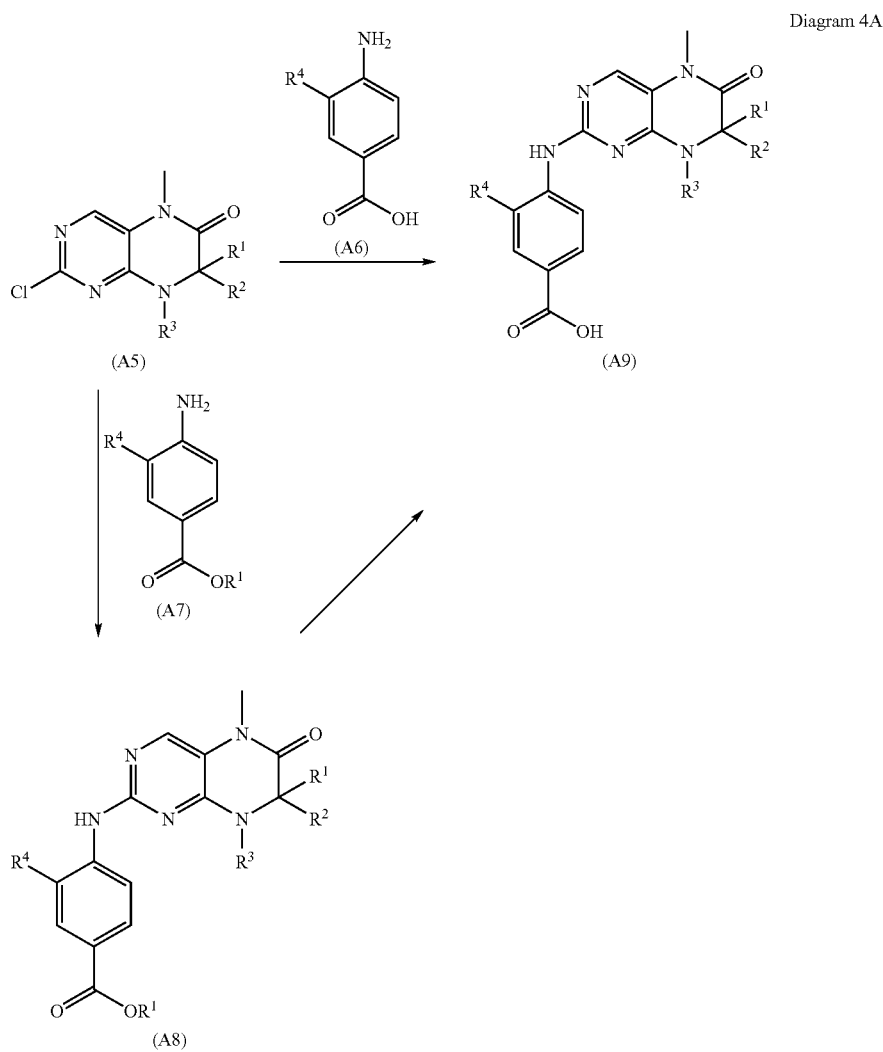

Diagram 4A

For example, in variant 4.1 A, 1 equivalent of the compound (A5) and 1 to 3 equivalents, preferably about 2 equivalents of the compound (A6) are heated without a solvent or in an organic solvent such as for example sulpholane, dimethylformamide, dimethylacetamide, toluene, N-methylpyrrolidone, dimethylsulphoxide or dioxane, preferably sulpholane, for 0.1 to 4 hours, preferably 1 hour, at 100 to 220° C., preferably at about 160° C. After cooling, the product (A9) is crystallised by the addition of organic solvents or mixtures of solvents, e.g. diethylether/methanol, ethyl acetate, methylene chloride, or diethylether, preferably diethylether/methanol 9/1, or purified by chromatography.

For example, in variant 4.2 A, 1 equivalent of the compound (A5) and 1 to 3 equivalents of the compound (A6) are stirred with acid, for example 1-10 equivalents of 10-38% hydrochloric acid and/or an alcohol, for example ethanol, propanol, butanol, preferably ethanol, at reflux temperature for 1 to 48 hours, preferably about 5 hours.

The product precipitated (A9) is filtered off and optionally washed with water, dried and crystallised from a suitable organic solvent.

For example, in variant 4.3 A, 1 equivalent of the compound (A5) and 1 to 3 equivalents of the compound (A7) are dissolved in a solvent, for example toluene or dioxane and combined with a phosphine ligand, for example 2,2"-bis-(diphenylphosphino)-1,1"-binaphthyl and a palladium catalyst, for example tris(dibenzylidene-acetone)-dipalladium(0) and a base, for example caesium carbonate, and refluxed for 1-24 h, preferably 17 h. The reaction mixture is purified for example over silica gel and the product (A8) is isolated from the solution or obtained by suitable crystallisation.

The product (A8) is dissolved in a suitable solvent, for example dioxane and mixed with acid, for example semiconcentrated hydrochloric acid, for example in the ratio of solvent to acid of 3:1. Then the mixture is refluxed for 1-48 h, for example 12 h, and the precipitate formed is isolated. If desired the product (A9) is purified by crystallisation.

Step 5A

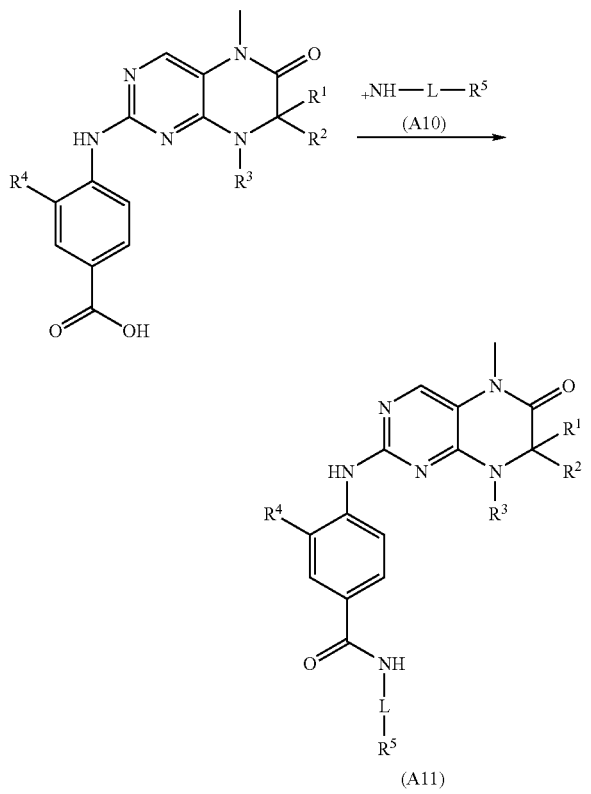

Diagram 5A (A11)

Variant 5.1 A:

For example, 1 equivalent of the compound (A9) is dissolved with 1 equivalent of an activating reagent, e.g. O-benzotriazolyl-N,N,N'',N''-tetramethyluronium tetrafluoroborate (TBTU) and a base, for example 1.5 equivalents of diisopropylethylamine (DIPEA) in an organic diluent, for example dichloromethane, tetrahydrofuran, dimethylformamide, N-methylpyrrolidone, dimethylacetamide, preferably dichloromethane or dimethylformamide. After the addition of 1 equivalent of the amine (A10) the reaction mixture is stirred for 0.1 to 24 hours, preferably about 2 hours at 20° C. to 100° C. The product of formula (A11) is obtained for example by crystallisation or chromatographic purification.

The new compounds of general formula (I) may be synthesised analogously to the following examples of synthesis. These Examples are, however, intended only as examples of procedures to illustrate the invention further, without restricting the invention to their subject matter.

The preparation of some intermediate compounds used to synthesise the examples is also described hereinafter.

Preparation of the Acids

To synthesise the compounds of Examples 94 and 95 first an intermediate

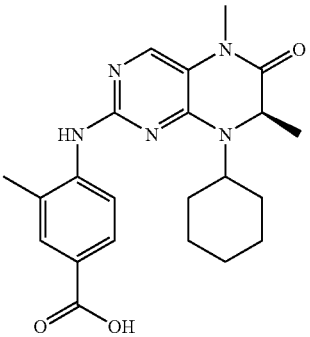

Z1 compound Z1
is prepared as described hereinafter.

50.0 g (0.48 mol) of D-alanine methyl ester x HCl and 49.1 g (0.50 mol) cyclohexanone were placed in 300 mL dichloromethane and then combined with 41.0 g (0.50 mol) sodium acetate and 159.0 g (0.75 mol) sodium triacetoxyborohydride. the mixture was stirred overnight and then 300 mL of 10% sodium hydrogen carbonate solution were added. The aqueous phase was extracted with dichloromethane. The combined organic phases were washed with 10% sodium hydrogen carbonate solution, dried over $Na_2SO_4$ and evaporated down.

Yield: 72.5 g of a compound Z1a (clear liquid)

72.5 g of the compound Z1a were placed in 500 mL water and 76.6 g (0.39 mol) of 2,4-dichloro-5-nitropyrimidine in 500 mL diethyl ether were added. At a temperature of −5° C. 100 mL 10% potassium hydrogen carbonate solution were added dropwise. The mixture was stirred for 3 h at −5° C. and for a further 12 h at ambient temperature. The organic phase was separated off and dried over $Na_2SO_4$. On evaporation the product crystallised out.

Yield: 48.0 g of a compound Z1b (yellow crystals)

48.0 g of the compound Z1b were dissolved in 350 mL glacial acetic acid and heated to 60° C. 47.5 g of iron powder were added, while the temperature rose to 105° C. The reaction mixture was stirred for three hours at 80° C., then filtered hot through cellulose and evaporated down. The residue was stirred in water and ethyl acetate, suction filtered and the light-grey precipitate was washed with ethyl acetate. The filtrate was washed with dilute ammonia and water, the organic phase was dried over $Na_2SO_4$, filtered through activated charcoal and evaporated down. Some more light-grey solid was obtained.

Yield: 29.5 g of a compound Z1c (light-grey crystals)

32.1 g of the compound Z1c were placed in 300 mL dimethylacetamide and combined with 13 mL (0.2 mol) methyl iodide. At –5° C. 6.4 g (0.16 mol) sodium hydride as a 60% dispersion in mineral oil was added batchwise. After 2 h the reaction mixture was poured onto 800 mL ice water. The precipitate formed was suction filtered and washed with petroleum ether.

Yield: 33.0 g of a compound Z1d (beige crystals)

4.0 g of the compound Z1d and 2.3 g (15 mmol) 4-amino-3-methylbenzoic acid were suspended in 50 mL ethanol and 120 mL water, combined with 2 mL conc. hydrochloric acid and refluxed for 48 h. The precipitate formed on cooling was suction filtered and washed with water, ethanol and diethyl ether.

Yield: 2.9 g of a compound Z1 (colourless crystals)

To synthesise the compounds Example 188 and Example 203 first of all an intermediate compound Z2

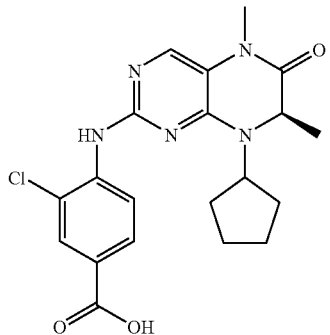

is prepared as described below.

A solution of 128.2 g (0.83 mol) D-alanine ethyl ester x HCl and 71.5 g (0.85 mol) cyclopentanone in 1500 mL dichloromethane was combined with 70.1 (0.85 mol) sodium acetate and 265.6 g (1.25 mol) sodium triacetoxyborohydride. The reaction mixture was stirred for 12 h and then poured into 1.5 L of a 10% sodium hydrogen carbonate solution. The aqueous phase was extracted with dichloromethane. The combined organic phases were dried over $Na_2SO_4$ and evaporated down.

Yield: 143.4 g of a compound Z2a (colourless oil)

66.0 g of the compound Z2a were placed in 500 mL water and combined with 85.0 g (0.44 mol) 2,4-dichloro-5-nitropyrimidine in 500 mL diethyl ether. At –5° C. 100 mL 10% potassium hydrogen carbonate solution were added dropwise and the reaction mixture was stirred for 48 h at ambient temperature. The aqueous phase was extracted with diethyl ether, the combined organic phases were dried over $Na_2SO_4$ and evaporated down. The dark red solid was stirred with petroleum ether and suction filtered.

Yield: 88.0 g of a compound Z2b (yellow crystals)

88.0 g of the compound Z2b were dissolved in 1000 mL glacial acetic acid and at 60° C. combined batchwise with 85 g iron powder, while the temperature rose to 110° C. It was stirred for 1 h at 60° C., then suction filtered hot through cellulose and evaporated down. The brown solid was stirred with 700 mL water and suction filtered.

Yield: 53.3 g of a compound Z2c (light brown crystals)

53.3 g of the compound Z2c were dissolved in 300 mL dimethylacetamide and combined with 13 mL (0.21 mol) methyl iodide. At –5° C. 5.0 g (0.21 mol) sodium hydride as a 60% dispersion in mineral oil were added batchwise. After 12 h the reaction mixture was poured onto 1000 mL ice water and the precipitate formed was suction filtered.

Yield: 40.0 g of a compound Z2d (colourless crystals)

4.0 g of the compound Z2d and 2.8 g (16 mmol) 4-amino-3-chlorbenzoic acid were suspended in 25 mL ethanol and 60 mL water, combined with 3 mL conc. hydrochloric acid and refluxed for 43 h. The precipitate formed on cooling was suction filtered and washed with water, ethanol and diethyl ether.

Yield: 0.9 g of a compound Z2 (colourless crystals)

To synthesise the compounds of Examples 19, 21, 22, 23, 45, 55, 58, 116, 128, 131, 133, 134, 136, 138, 177, 217, 231, 239, 46, 184, 166 and 187 first of all an intermediate compound Z3

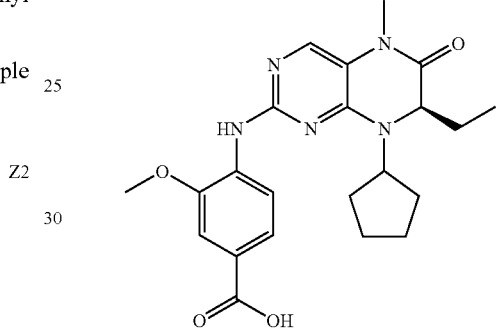

is prepared as described below.

54.0 g (0.52 mol) D-2-aminobutyric acid were suspended in 540 mL methanol and slowly combined with 132 g (1.1 mol) thionyl chloride while cooling with ice. The mixture was refluxed for 1.5 h and then evaporated down. The oil remaining was combined with 540 mL tert-butylmethylether and the colourless crystals formed were suction filtered.

Yield: 78.8 g of a compound Z3a (colourless crystals)

74.2 g of the compound Z3a and 43.5 mL (0.49 mol) cyclopentanone were dissolved in 800 mL dichloromethane. After the addition of 40.0 g (0.49 mol) sodium acetate and 150.0 g (0.71 mol) sodium triacetoxyborohydride at 0° C. the mixture was stirred for 12 h at ambient temperature and then 500 mL of 20% sodium hydrogen carbonate solution were added. The aqueous phase was extracted with dichloromethane. The combined organic phases were washed with water, dried over $MgSO_4$ and evaporated down.

Yield: 85.8 g of a compound Z3b (light yellow oil)

40.0 g of the compound Z3b and 30.0 g (0.22 mol) potassium carbonate were suspended in 600 mL acetone and combined with 45.0 g (0.23 mol) 2,4-dichloro-5-nitropyrimidin in 200 mL acetone while cooling with ice. After 12 h a further 5.0 g 2,4-dichloro-5-nitropyrimidin were added and stirred for 3 h. The reaction mixture was evaporated down, taken up in 800 mL ethyl acetate and 600 mL water and the aqueous phase was extracted with ethyl acetate. The combined organic phases were washed with water, dried over $MgSO_4$ and evaporated down.

Yield: 75.0 g of a compound Z3c (brown oil)

100 g of the compound Z3c were dissolved in 650 mL glacial acetic acid and at 70° C. 20 g of iron powder were added batchwise. The mixture was stirred for 1 h at 70° C., then for 1.5 h at 100° C. and then filtered hot through kieselgur. The reaction mixture was evaporated down, taken up in methanol/dichloromethane, applied to silica gel and purified with ethyl acetate by Soxhlet extraction. The solvent was removed and the residue stirred with methanol.

Yield: 30.0 g of a compound Z3d (light brown crystals)

25.0 g of the compound Z3d and 6.5 mL (0.1 mol) methyl iodide were placed in 250 mL dimethylacetamide and at −10° C. 3.8 g (0.95 mol) sodium hydride as a 60% dispersion in mineral oil was added. It was stirred for 20 min at 0° C., then for 30 min at ambient temperature and finally ice was added. The reaction mixture was evaporated down and combined with 300 mL water. The precipitate formed was suction filtered and washed with petroleum ether.

Yield: 23.0 g of a compound Z3e (colourless solid)

6.0 g of the compound Z3e and 5.1 g (31 mmol) 4-amino-3-methoxybenzoic acid were suspended in 90 mL ethanol and 350 mL water, combined with 3.5 mL conc. hydrochloric acid and refluxed for 48 h. The reaction mixture was evaporated down, the residue stirred with methanol/diethyl ether and the precipitate formed was suction filtered.

Yield: 6.3 g of a compound Z3 (light beige crystals)

To synthesise the compound of Examples 81, 82, 93, 137 first of all an intermediate compound Z4 evaporated down. After the addition of diethyl ether additional product crystallised out.

Yield: 4.0 g of a compound Z4c (yellow crystals)

7.8 g of the compound Z4c and 2.6 mL (0.04 mol) methyl iodide were dissolved in 100 mL dimethylacetamide and at −5° C. 1.5 g (0.04 mol) sodium hydride were added batchwise as a 60% dispersion in mineral oil. After 2 h the reaction mixture was poured onto ice water and the precipitate formed was suction filtered.

Yield: 7.5 g of a compound Z4d (light brown crystals)

3.0 g of the compound Z4d and 1.9 g (11 mmol) 4-amino-3-methoxybenzoic acid were suspended in 40 mL ethanol and 80 mL water, combined with 2 mL conc. hydrochloric acid and refluxed for 20 h. A further 0.5 g of 4-amino-3-methoxybenzoic acid were added and refluxed for 48 h. The precipitate formed on cooling was suction filtered and washed with water, ethanol and diethyl ether.

Yield: 2.1 g of a compound Z4 (colourless crystals) m.p.: 222-223° C.

To synthesise the compounds of Examples 162, 43, 53, 161, 202, 211, 215 and 212 first of all an intermediate compound Z5

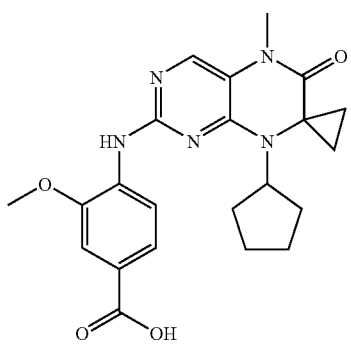

Z4

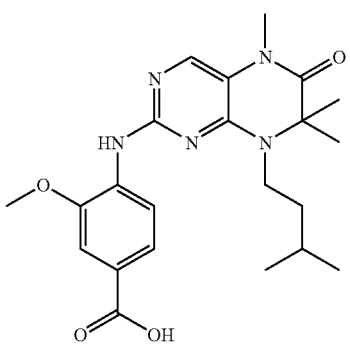

Z5 is prepared as described below.

25.0 g (0.19 mol) of ethyl 1-aminocyclopropane-1-carboxylate x HCl and 16.8 g (0.20 mol) of cyclopentanone were dissolved in 300 mL of dichloromethane and combined with 16.4 g (0.20 mol) of sodium acetate and 61.7 g (0.29 mol) of sodium triacetoxyborohydride. It was stirred overnight and the reaction mixture was then poured onto 400 mL of 10% sodium hydrogen carbonate solution. The aqueous phase was extracted with dichloromethane. The combined organic phases were dried over Na$_2$SO$_4$ and evaporated down.

Yield: 34.5 g of a compound Z4a (colourless oil)

42.5 g (0.22 mol) of 2,4-dichloro-5-nitropyrimidine in 350 mL of diethyl ether were added to a mixture of 34.5 g of the compound Z4a in 350 mL water. At −5° C. the mixture was combined with 80 mL 10% potassium hydrogen carbonate solution and stirred overnight at ambient temperature. The aqueous phase was extracted with diethyl ether. The combined organic phases were dried over Na$_2$SO$_4$ and evaporated down.

Yield: 53.8 g of a compound Z4b (brown oil)

20.1 g of the compound Z4b were dissolved in 200 mL glacial acetic acid and combined batchwise at 60° C. with 19.1 g iron powder, during which time the temperature rose to 100° C. The mixture was stirred for 3 h at 60° C., then suction filtered through cellulose and evaporated down. The residue was stirred in water and ethyl acetate and the yellow precipitate was suction filtered. The filtrate was washed with dilute ammonia and water, the organic phase dried over Na$_2$SO$_4$ and is prepared as described below.

A mixture of 73.4 mL (0.5 mol) ethyl 2-bromoisobutyrate, 87.1 mL (0.75 mol) of 3-methyl-1-butylamine, 82.5 g (0.6 mol) sodium iodide and 76.0 g (0.6 mol) of potassium carbonate in 1000 mL ethyl acetate was refluxed for 3 days. Any salts present were filtered off and the filtrate evaporated down.

Yield: 97.0 g of a compound Z5a (red oil)

49.0 g (0.25 mol) of 2,4-dichloro-5-nitropyrimidine and 38.3 g (0.28 mol) of potassium carbonate were suspended in 500 mL acetone and at 0° C. combined with 93.0 g of the compound Z5a in 375 mL acetone. The reaction mixture was stirred overnight at ambient temperature, filtered and evaporated down. The residue dissolved in ethyl acetate was washed with water and the organic phase dried over MgSO$_4$ and evaporated down.

Yield: 102.7 g of a compound Z5b (brown oil)

22.7 g of the compound Z5b were dissolved in 350 mL glacial acetic acid and at 60° C. combined batchwise with 17.4 g iron powder. After the addition had ended the mixture was refluxed for 0.5 h, filtered hot and evaporated down. The residue was taken up in 200 mL dichloromethane/methanol (9:1) and washed with sodium chloride solution. The organic phase was suction filtered through kieselguhr, dried over MgSO$_4$, evaporated down and purified by column chromatography (eluant: ethyl acetate/cyclohexane 1:1).

Yield: 1.9 g of a compound Z5c (colourless crystals)

1.9 g of the compound Z5c were dissolved in 32 mL dimethylacetamide and while cooling with ice combined with 0.3 g (7 mmol) sodium hydride as a 60% dispersion in mineral oil. After 10 min 0.5 mL (7 mmol) methyl iodide were added and stirred for 3 h at ambient temperature. The reaction mixture was evaporated down and combined with water. The precipitate formed was suction filtered and washed with petroleum ether.

Yield: 1.6 g of a compound Z5d (colourless crystals)

14.0 g of the compound Z5d and 10.0 g (0.06 mol) 4-amino-3-methoxybenzoic acid were suspended in 200 mL dioxane and 80 mL water, combined with 10 mL conc. hydrochloric acid and refluxed for 40 h. The precipitate formed on cooling was suction filtered and washed with water, dioxane and diethyl ether.

Yield: 13.9 g of a compound Z5 (colourless crystals)

To synthesise the compounds of Examples 88, 194, 229 and 89 first of all an intermediate compound Z6

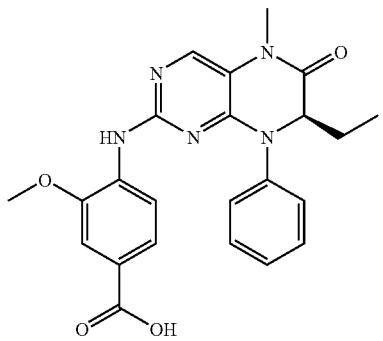

Z6 is prepared as described below.

6.0 g (0.06 mol) L-2-aminobutyric acid was placed in 80 mL 0.5 M sulphuric acid and at 0° C. combined with 5.5 g (0.08 mol) sodium nitrite in 15 mL water. The reaction mixture was stirred for 22 h at 0° C., combined with ammonium sulphate and filtered. The filtrate was extracted with diethyl ether and the combined organic dried over $MgSO_4$ and evaporated down.

Yield: 6.0 g of a compound Z6a (yellow oil)

200 mL methanol were combined successively with 65.0 mL (0.89 mol) thionyl chloride and 76.0 g of the compound Z6a in 50 mL methanol while cooling with ice. The resulting mixture was stirred for 1 h at 0° C. and 2 h at ambient temperature and then the methanol and remaining thionyl chloride were eliminated in vacuo at 0° C.

Yield: 40.0 g of a compound Z6b (yellow oil)

30.0 mL (0.17 mol) of trifluoromethanesulphonic acid anhydride were placed in 150 mL dichloromethane and while cooling with ice a solution of 20.0 g of the compound Z6b and 14.0 mL (0.17 mol) pyridine in 50 mL dichloromethane was added within one hour. The mixture was stirred for 2 h at ambient temperature, any salts formed were suction filtered and then washed with 100 mL water. The organic phase was dried over $MgSO_4$ and evaporated down.

Yield: 42.0 g of a compound Z6c (light yellow oil)

42.0 g of the compound Z6c in 200 mL dichloromethane was added dropwise within one hour to a solution of 15.5 mL (0.17 mol) of aniline and 24.0 mL (0.17 mol) of triethylamine in 400 mL dichloromethane while cooling with ice. The mixture was stirred for 1 h at ambient temperature and a further 2 h at 35° C. The reaction mixture was washed with water, dried over $MgSO_4$ and evaporated down. The residue remaining was purified by distillation (95-100° C., $1*10^{-3}$ mbar).

Yield: 14.0 of a compound Z6d (colourless oil)

14.0 g of the compound Z6d and 16.0 g (0.1 mol) potassium carbonate were suspended in 100 mL acetone and at 10° C. combined with 16.0 g (0.08 mol) of 2,4-dichloro-5-nitropyrimidine. The mixture was stirred for 4 h at 40° C., any salts formed were suction filtered and the filtrate evaporated down. The residue was taken up in 300 mL ethyl acetate and washed with water. The organic phase was dried over $MgSO_4$ and evaporated down.

Yield: 31.0 g of a compound Z6e (brown oil)

31.0 g of the compound Z6e were dissolved in 200 mL glacial acetic acid and at 60° C. combined batchwise with 10 g iron powder, during which time the temperature rose to 85° C. The mixture was stirred for a further hour at 60° C., filtered through kieselguhr and evaporated down. The residue was stirred with methanol.

Yield: 4.5 g of a compound Z6f (brown crystals)

At −20° C. 0.6 g (16 mmol) of sodium hydride as a 60% dispersion in mineral oil were added batchwise to a mixture of 4.5 g of the compound Z6f and 1.0 mL (16 mmol) methyl iodide in 100 mL dimethylacetamide. After 1 h the reaction mixture was combined with 50 mL water and evaporated down. The residue was stirred with 200 mL water, the precipitate is suction filtered and washed with petroleum ether.

Yield: 4.5 g of a compound Z6g (colourless crystals)

A suspension of 1.5 g of the compound Z6g and 1.4 g (8 mmol) of methyl 4-amino-3-methoxybenzoate in 30 mL toluene was combined with 0.4 g (0.6 mmol) of 2,2"-bis-(diphenylphosphino)-1,1"-binaphthyl, 0.23 g (0.3 mmol) of tris (dibenzylideneacetone)-dipalladium(0) and 7.0 g (21 mmol) of caesium carbonate and refluxed for 17 h. The reaction mixture was applied to silica gel and purified by column chromatography (eluant:dichloromethane/methanol 9:1).

Yield: 1.7 g of a compound Z6h (yellow crystals)

1.7 g of the compound Z6h were dissolved in 50 mL dioxane, combined with 15 mL of semiconc. hydrochloric acid and refluxed for 12 h. After cooling the precipitate formed was suction filtered.

Yield: 1.1 g of a compound Z6 (colourless solid)

To synthesise the compound of Examples 26, 20, 32, 56, 101, 112, 209 first of all an intermediate compound Z7 is prepared as described below.

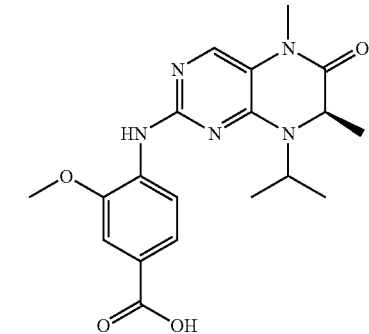

50.0 g (0.36 mol) D-alanine methyl ester x HCl was suspended in 500 mL of dichloromethane and 35 mL of acetone and combined with 30.0 g (0.37 mol) of sodium acetate and 80.0 g (0.38 mol) of sodium triacetoxyborohydride. The mixture was stirred for 12 h and then poured onto 400 mL of 10% sodium hydrogen carbonate solution. The organic phase was dried over $Na_2SO_4$ and evaporated down.

Yield: 51.0 g of a compound Z7a (yellow oil)

A suspension of 51.0 g of the compound Z7a in 450 mL water was combined with 80.0 g (0.41 mol) of 2,4-dichloro-5-nitropyridine in 450 mL of diethyl ether. At −5° C. 100 mL of 10% potassium hydrogen carbonate solution were added dropwise. The reaction mixture was stirred for 3 h, the organic phase dried over $Na_2SO_4$ and evaporated down.

Yield: 74 g of a compound Z7b (yellow oil)

18.6 g of the compound Z7b were dissolved in 200 mL glacial acetic acid and at 60° C. combined batchwise with 20.0 g iron powder. The mixture was stirred for 2 h at 60° C. and then suction filtered through cellulose. The residue was dissolved in ethyl acetate and washed with water and conc. ammonia. The organic phase was dried over $Na_2SO_4$ and evaporated down. The residue was crystallised from diethyl ether.

Yield: 9.8 g of a compound Z7c (colourless crystals)

17.0 g of the compound Z7c and 7 mL (0.1 mol) methyl iodide were dissolved in 200 mL dimethylacetamide and at −5° C. combined with 4.0 g (0.1 mol) of sodium hydride as a 60% dispersion in mineral oil. The reaction mixture was stirred for 30 min and then poured onto 300 mL ice water. The precipitate formed was suction filtered and stirred with petroleum ether.

Yield: 14.8 g of a compound Z7d (beige crystals)

0.9 g of the compound Z7d and 1.5 g (9 mmol) 4-amino-3-methoxybenzoic acid were heated to 210° C. for 30 min. After cooling the residue was stirred with ethyl acetate and the precipitate obtained was suction filtered.

Yield: 1.2 g of a compound Z7 (grey crystals)

The following acids were prepared, for example, analogously to the methods of synthesis described:

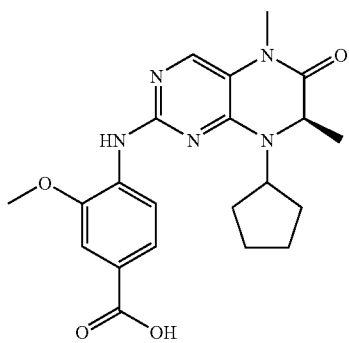

Z8

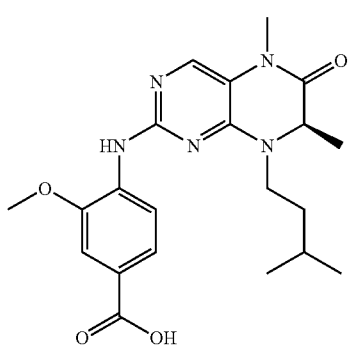

Z9

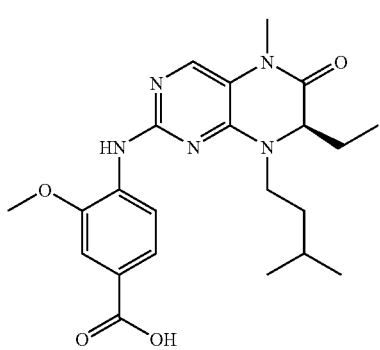

Z10

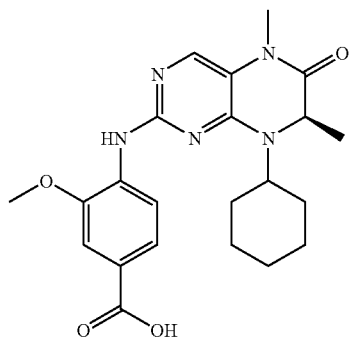

Z11

Synthesis of the amino components L-R5

The following amines were obtained as follows:

1,1-dimethyl-2-dimethylamino-1-yl-ethylamine and 1,1-dimethyl-2-piperidin-1-yl-ethylamine

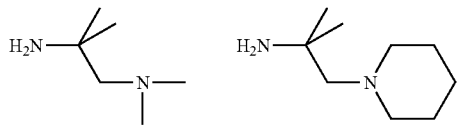

The compounds were prepared according to the following references: a) S. Schuetz et al. *Arzneimittel-Forschung* 1971, 21, 739-763 b) V. M. Belikov et al. *Tetrahedron* 1970, 26, 1199-1216. c) E. B. Butler and McMillan *J. Amer. Chem. Soc.* 1950, 72, 2978.

Other amines were prepared as follows, in a modified manner compared with the literature described above.

1,1-dimethyl-2-morpholin-1-yl-ethylamine

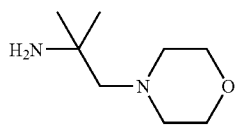

8.7 mL morpholine and 9.3 mL 2-nitropropane were prepared, while cooling with ice, 7.5 mL formaldehyde (37%) and 4 mL of a 0.5 mol/L NaOH solution were slowly added dropwise (<10° C.). Then the mixture was stirred for 1 h at 25° C. and 1 h at 50° C. The solution was treated with water and ether and the aqueous phase was extracted 3× with ether. The combined org. phase was dried over NaSO4 and combined with HCl in dioxane (4 mol/l), the precipitate formed was suction filtered.

Yield: 21.7 of white powder 5 g of the white powder were dissolved in 80 mL methanol and with the addition of 2 g RaNi treated with hydrogen at 35° C. and 50 psi for 40 minutes. This yielded 3.6 g of 1,1-dimethyl-2-morpholin-1-yl-ethylamine.

The following amines were prepared by this method:

1,1-dimethyl-N-methylpiperazin-1-yl-ethylamine

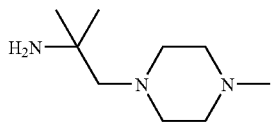

1,1-dimethyl-2-pyrrolidin-1-yl-ethylamine

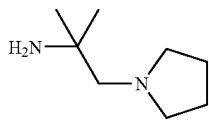

Synthesis of 1,3-dimorpholin-2-amino-propane

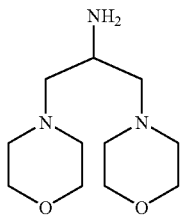

5 g of 1,3 Dimorpholine-2-nitropropane obtained from Messrs. Aldrich was dissolved in 80 mL methanol and treated with hydrogen for 5.5 h at 30° C. and 50 psi with the addition of 2 g RaNi. This yielded 4.2 g of 1,3 dimorpholin-2-amino-propane.

4-Aminobenzylmorpholine

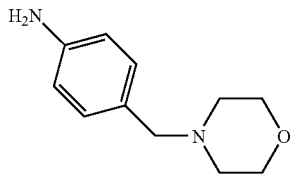

The preparation of this amine is described in the following reference:
S. Mitsuru et al. *J. Med. Chem.* 2000, 43, 2049-2063

4-amino-1-tetrahydro-4H-pyran-4-yl-piperidine

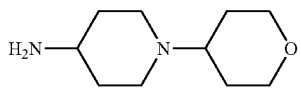

20 g (100 mmol) of 4-tert-butyloxycarbony-aminopiperidine were dissolved in 250 mL $CH_2Cl_2$ and stirred for 12 h at RT with 10 g (100 mmol) tetrahydro-4H-pyran-4-one and 42 g (200 mmol) $NaBH(OAc)_3$. Then water and potassium carbonate were added, the org. phase was separated off, dried and the solvent was eliminated in vacuo. The residue was dissolved in 200 mL $CH_2Cl_2$ and stirred for 12 h at RT with 100 mL trifluoroacetic acid. The solvent was eliminated in vacuo, the residue taken up with $CHCl_3$ and evaporated down again, then taken up in acetone and the hydrochloride was precipitated with ethereal HCl. Yield: 14.3 g (56%).

cis- and trans-4-morpholino-cyclohexylamine

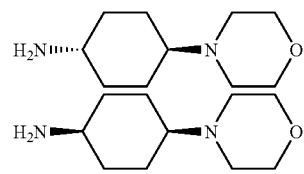

Dibenzyl-4-morpholino-cyclohexylamine 3.9 g (30 mmol) of 4-dibenzylcyclohexanone were dissolved in 100 mL of $CH_2Cl_2$ and stirred for 12 h at RT with 3.9 g (45 mmol) of morpholine and 9.5 g (45 mmol) $NaBH(OAc)_3$. Then water and potassium carbonate were added, the org. phase was separated off, dried and the solvent was eliminated in vacuo. The residue was purified through a silica gel column (about 20 mL silica gel; about 500 mL of ethyl acetate 90/methanol 10+1% conc. ammonia). The appropriate fractions were evaporated down in vacuo. Yield: 6.6 g (60%) of cis-isomer and 2 g (18%) of trans-isomer.

Alternatively the trans-dibenzyl-4-morpholino-cyclohexylamine may be prepared by the following method:

33 g (112 mmol) of 4-dibenzylcyclohexanone were dissolved in 300 mL MeOH, combined with 17.4 g (250 mmol) of hydroxylamine hydrochloride and stirred for 4 h at 60° C. The solvent was evaporated down in vacuo, combined with 500 mL water and 50 g potassium carbonate and extracted twice with 300 mL of dichloromethane. The org. phase was dried, evaporated down in vacuo, the residue was crystallised from petroleum ether, dissolved in 1.5 L of EtOH and heated to 70° C. 166 g of sodium were added batchwise and the mixture was refluxed until the sodium dissolved. The solvent is eliminated in vacuo, the residue combined with 100 mL water and extracted twice with 400 mL of ether. The org. phase is washed with water, dried, evaporated down in vacuo and the trans isomer is isolated using a column (about 1.5 L silica gel; about 2 L of ethyl acetate 80/methanol 20+2% conc. ammonia). Yield: 12.6 g (41.2%).

6.8 g (23 mmol) of trans-1-amino-4-dibenzylaminocyclohexane was dissolved in 90 mL of DMF and stirred for 8 h at 100° C. with 5 mL (42 mmol) of 2,2"-dichloroethyl ether and 5 g of potassium carbonate. After cooling 30 mL of water was added, the precipitated crystals were suction filtered and purified through a short column (about 20 mL silica gel, about 100 mL ethyl acetate). The residue is crystallised from methanol and conc. HCl as the dihydrochloride. Yield: 7.3 g (72.4%).

trans-4-morpholino-cyclohexylamine 7.2 g (16.4 mmol) of trans-dibenzyl-4-morpholino-cyclohexylamine were dissolved in 100 mL of MeOH and hydrogenated on 1.4 g of Pd/C (10%) at 30-50° C. The solvent was eliminated in vacuo and the residue was crystallised from ethanol and conc. HCl. Yield: 3.9 g (93%); m.p. 312° C.

The cis isomer can be prepared analogously.

cis- and trans-4-piperidino-cyclohexylamine

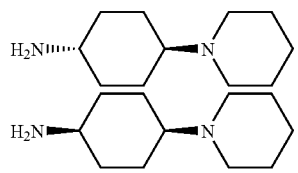

trans-dibenzyl-4-piperidino-cyclohexylamine 2.0 g (6.8 mmol) of trans-1-amino-4-dibenzylaminocyclohexane (see Example 2) was dissolved in 50 mL DMF and stirred for 48 h at RT with 1.6 g (7 mmol) of 1,5-dibromopentane and 2 g of potassium carbonate. The mixture was cooled, combined with water, extracted twice with 100 mL of dichloromethane, dried and the solvent was eliminated in vacuo. The residue is purified over a column (about 100 mL silica gel, about 500 mL ethyl acetate 80/methanol 20+1% conc. ammonia). The desired fractions were evaporated down in vacuo and crystallised from petroleum ether. Yield: 1.2 g (49%).

trans-4-piperidino-cyclohexylamine 1.7 g (4.8 mmol) of trans-dibenzyl-4-piperidino-cyclohexylamine were dissolved in 35 mL MeOH and hydrogenated on 350 mg of Pd/C (10%) at 20° C. The solvent was eliminated in vacuo and the residue crystallised from ethanol and conc. HCl.

Yield: 1.1 g (78%).

The cis isomer may be prepared analogously.

cis- and trans-4-(4-phenyl-piperazin-1-yl)-cyclohexylamine

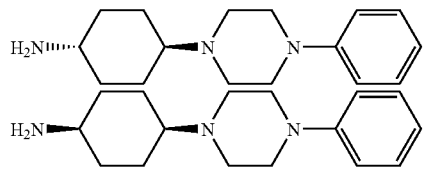

4.1 g (25.3 mmol) of 4-dibenzylcyclohexanone was dissolved in 50 mL of dichloromethane and stirred for 12 h at RT with 7.4 g (25.3 mmol) of N-phenylpyperazine and 7.4 g (35 mmol) of NaBH(OAc)$_3$. Then water and potassium carbonate were added, the org. phase was separated off, dried and the solvent was eliminated in vacuo. The residue was purified over a silica gel column (ethyl acetate 80/methanol 20+0.5% conc. ammonia). Yield: 1.7 g (15.8%) of cis-isomer and 0.27 (2.5%) of trans-isomer.

trans-4-(4-phenyl-piperazin-1-yl)-cyclohexylamine 270 mg (0,61 mmol) of trans-dibenzyl-[4-(4-phenyl-piperazin-1-yl)-cyclohexyl]-amine were dissolved in 5 mL MeOH and hydrogenated on 40 mg of Pd/C (10%) at 20-30° C. The solvent was eliminated in vacuo and the residue crystallised from ethanol and conc. HCl. Yield: 110 mg (69%).

The cis isomer may be prepared analogously.

cis- and trans-4-(4-cyclopropylmethyl-piperazin-1-yl)-cyclohexylamine

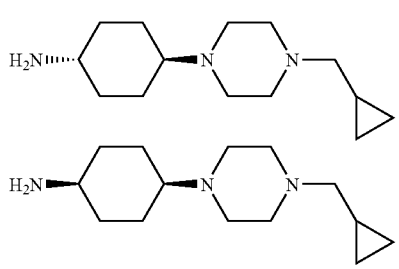

9.8 g (33.4 mmol) of 4-dibenzylcyclohexanone was dissolved in 100 mL dichloromethane and stirred for 12 h at RT with 5.6 g (40 mmol) of N-cyclopropylmethylpiperazine and 8.5 g (40 mmol) of NaBH(OAc)$_3$. Then water and potassium carbonate were added, the org. phase was separated off, dried and the solvent was eliminated in vacuo. The residue was purified over a silica gel column (about 50 mL silica gel, about 3 L ethyl acetate 95/methanol 5+0.25% conc. ammonia. The appropriate fractions were evaporated down in vacuo. The faster eluting cis compound crystallised from ethyl acetate. The trans-compound was crystallised from ethanol+conc. HCl. Yield: 8.5 g (61%) cis-isomer and 2.2 (13%) trans-isomer.

cis-4-(4-cyclopropylmethyl-piperazin-1-yl)-cyclohexylamine 8.5 g (20 mmol) of cis-dibenzyl-[4-(4-cyclopropylmethyl-piperazin-1-yl)-cyclohexyl]-amine were dissolved in 170 mL MeOH and hydrogenated on 1.7 g Pd/C (10%) at 30-50° C. The solvent was eliminated in vacuo and the residue was crystallised from ethanol and conc. HCl. Yield: 4.4 g (91%).

The trans-isomer may be prepared analogously.

SYNTHESIS OF THE EXAMPLES

Example 152

0.15 g of the compound Z10, 0.14 g TBTU, 0.13 mL DIPEA were dissolved in dichloromethane and stirred for 20 minutes at 25° C. Then 90 µL 1-(3-aminopropyl)-4-methylpiperazine was added and stirred for a further 2 hours at 25° C. The solution was then diluted with dichloromethane and extracted with water. The product was precipitated by the addition of petroleum ether, ether and ethyl acetate to the organic phase. Yield: 0.16 g of beige solid Example 164

0.10 g of the compound Z10, 0.1 g TBTU, 0.08 mL DIPEA were dissolved in 4 mL dichloromethane and stirred for 20 minutes at 25° C. Then 44 µL dimethylaminopropylamine were added and stirred for a further 2 hours at 25° C. The solution was then diluted with dichloromethane and extracted with water. The product was precipitated by the addition of petroleum ether, ether and acetone to the organic phase. Yield: 0.08 g yellow solid.

Example 242

0.15 g of the compound Z10, 0.14 g TBTU, 0.13 mL DIPEA were dissolved in 5 mL dichloromethane and stirred for 20 minutes at 25° C. Then 75 µL 1-(2-aminoethyl) piperidine were added and stirred for a further 2 hours at 25° C. The solution was then diluted with dichloromethane and extracted with water. The product was precipitated by the addition of petroleum ether, ether and ethyl acetate to the organic phase. Yield: 0.14 g yellow solid.

Example 188

0.1 g of the compound Z2, 0.09 g TBTU, 0.05 mL DIPEA were dissolved in 15 mL dichloromethane and stirred for 20 minutes at 25° C. Then 33 mg 1-methyl-4-aminopiperidin were added and the mixture was stirred for a further 3 hours at 25° C. The solution was extracted with 20 mL water, then evaporated down in vacuo. The product was crystallised using ether. Yield: 0.047 g of white crystals.

Example 203

0.1 g of the compound Z2, 0.09 g TBTU, 0.5 mL DIPEA were dissolved in 15 mL dichloromethane and stirred for 30 minutes at 25° C. Then 50 mg 4-amino-1-benzylpiperidin were added and the mixture was stirred for a further 3 hours at 25° C. The solution was extracted with 20 mL water, then evaporated down in vacuo. Then the residue was chromatographed over silica gel and the isolated product was crystallised with ether. Yield: 0.015 g of white crystals.

Example 94

0.17 g of the compound Z1, 0.19 g TBTU, 0.11 mL DIPEA were dissolved in 50 mL dichloromethane and stirred for 30 minutes at 25° C. Then 63 mg of 1-methyl-4-aminopiperidine were added and the mixture was stirred for a further 17 hours at 25° C. 50 mL of water and 1 g of potassium carbonate were added to the solution and the organic phase was separated off using a phase separation cartridge, then evaporated down in vacuo. Then the product was purified by silica gel chromatography and the purified product was crystallised with ether. Yield: 0.1 g of white crystals.

Example 95

0.17 g of the compound Z1, 0.19 g TBTU, 0.11 mL DIPEA were dissolved in 50 mL dichloromethane and stirred for 30 minutes at 25° C. Then 77 mg of exo-3-β-amino-tropane were added and the mixture was stirred for a further 17 hours at 25° C. 50 mL of water and 1 g of potassium carbonate were added to the solution and the organic phase was separated off using a phase separation cartridge, then evaporated down in vacuo. Then the product was purified by silica gel chromatography and the purified product was crystallised with ether. Yield: 0.03 g of white crystals.

Example 46

0.15 g of the compound Z3, 0.12 g TBTU, 0.12 mL DIPEA were dissolved in 5 mL dichloromethane and stirred for 30 minutes at 25° C. Then 50 mg 1-methyl-4-aminopiperidin were added and the mixture was stirred for a further 2.5 hours at 25° C. The solution was then extracted with water and then evaporated down. The residue was dissolved in warm ethyl acetate and crystallised from ether and petroleum ether. Yield: 0.025 g of white crystals. M.p.: 203° C. as the base

Example 80

0.2 g of the compound Z8, 0.2 g of TBTU, 0.1 mL of DIPEA were dissolved in 10 mL dichloromethane and stirred for 30 minutes at 25° C. Then 100 mg of 1-methyl-4-aminopiperidine were added and the mixture was stirred for a further 17 hours at 25° C. The solution was then extracted with a dilute potassium carbonate solution and evaporated down. The residue was crystallised using ether. Yield: 0.12 g of white crystals

Example 190

0.2 g of compound Z8, 0.2 g of TBTU, 0.3 mL of DIPEA were dissolved in 5 mL dichloromethane and stirred for 1 h at 25° C. Then 0.13 g of 4-amino-1-benzylpiperidine were added and the mixture was stirred for a further hour at 25° C. The solution was then diluted with 10 mL methylene chloride and extracted with 20 mL water. Then the product was purified over silica gel and crystallised from ethyl acetate and ether. Yield: 0.23 g of the compound Z8.

0.23 g of the benzylamine Z8 are dissolved in 10 mL methanol, combined with 50 mg of Pd/C and hydrogenated under 3 bar for 3 h at 25° C. By adding petroleum ether and ethyl acetate white crystals are produced. These are chromatographed over silica gel and crystallised from ethyl acetate and ether. Yield: 0.075 g of white crystals.

Example 196

0.1 g of compound Z10, 0.09 g of TBTU, 0.3 mL of DIPEA were dissolved in 4 mL of dichloromethane and stirred for 20 minutes at 25° C. Then 67 mg xx amine was added and stirred for a further 2 hours at 25° C. The solution was then diluted with dichloromethane and extracted with water. It was then chromatographed over silica gel and the residue was dissolved in acetone, combined with ethereal HCl and the precipitate formed was isolated. Yield: 0.09 g light yellow solid

Example 166

0.1 g of the compound Z10, 0.11 g of TBTU, 0.14 mL of DIPEA were dissolved in 2 mL dimethylformamide and stirred for 3 h at 50° C. Then 55 mg of 4-morpholinomethylphenylamine was added. The reaction mixture was then cooled to ambient temperature within 17 h. Then the dimethylformamide was eliminated in vacuo, the residue was taken up in dichloromethane and extracted with water. It was then chromatographed over silica gel and the product crystallised from ethyl acetate and ether. Yield: 0.06 g yellowish crystals

Example 81

0.2 g of the compound Z4, 0.2 g of TBTU, 0.1 mL of DIPEA were dissolved in 10 mL dichloromethane and stirred for 30 minutes at 25° C. Then 0.1 g of 1-methyl-4-aminopiperidine were added and the mixture was stirred for a further 17 hours at 25° C. The solution was then extracted with aqueous potassium carbonate solution and then evaporated down. The product was crystallised using ether. Yield: 0.16 g of white crystals.

Example 162

0.1 g of the compound Z5, 0.07 g of TBTU, 0.15 mL of DIPEA were dissolved in 5 mL dichloromethane and stirred for 20 minutes at 25° C. Then 0.04 g 1-methyl-4-aminopiperidine were added and the mixture was stirred for a further 2 hours at 25° C. The solution was then diluted with 15 mL dichloromethane and extracted with 20 mL water. The residue was dissolved in MeOH and acetone, combined with 1 mL ethereal HCl and evaporated down. A crystalline product was produced using ether, ethyl acetate and a little MeOH. Yield: 0.1 g of white crystals.

Example 88

0.1 g of the compound Z6, 0.12 g of TBTU, 0.12 mL of DIPEA were in 10 mL dichloromethane dissolved and stirred for 30 minutes at 25° C. Then 0.04 g of 1-methyl-4-aminopiperidine were added and the mixture was stirred for a further 2 hours at 25° C. The solution was then diluted with 10 mL dichloromethane and extracted with 10 mL water. A crystalline product was produced using ether, ethyl acetate and petroleum ether. Yield: 0.6 g of white crystals.

Example 89

0.1 g of the compound Z6, 0.08 g of TBTU, 0.08 mL of DIPEA were dissolved in 10 mL dichloromethane and stirred for 30 minutes at 25° C. Then 37 µL g N,N-dimethylneopentanediamine were added and the mixture was stirred for a further 2 hours at 25° C. The solution was then diluted with 10 mL dichloromethane and extracted with 10 mL water. The product was then chromatographed over silica gel and crystallised from ethyl acetate, ether and petroleum ether. Yield: 0.005 g of white crystals.

Example 26

0.15 g of the compound Z7, 0.16 g of TBTU, 1 mL of DIPEA were dissolved in 5 mL dichloromethane and stirred for 30 minutes at 25° C. Then 0.1 g 4-morpholinocyclohexylamine were added and the mixture was stirred for a further 17 hours at 25° C. The residue was then combined with 10 mL of 10% potassium carbonate solution, the precipitate was isolated and washed with water. It was then dissolved in dichloromethane and evaporated down again. The product was crystallised from ethyl acetate. Yield: 0.1 g of white crystals.

Example 9

150 mg of the compound Z9 and 93 mg of amine were dissolved in 5 mL dichloromethane and stirred with 160 mg of TBTU and 1 mL of DIPEA for 12 h at RT. The solvent was eliminated in vacuo, the residue was combined with 10 mL of 10% potassium carbonate solution. The precipitate was suction filtered, washed with water, taken up in dichloromethane, dried and the solvent eliminated in vacuo. The residue was crystallised from ethyl acetate. Yield: 82.0 mg; m.p. 253° C. (as base).

Example 16

150 mg of the compound Z8 and 73 mg of trans-4-piperidino-cyclohexylamine were dissolved in 5 mL dichloromethane and stirred with 160 mg (0.50 mmol) of TBTU and 1 mL of DIPEA for 12 h at RT. The solvent was eliminated in vacuo, the residue was combined with 10 mL of 10% potassium carbonate solution. The precipitate was suction filtered, washed with water, taken up in dichloromethane, dried and the solvent eliminated in vacuo. The residue was crystallised from ethyl acetate. Yield: 87.0 mg; m.p. 237° C. (as base).

Example 37

100 mg of the compound Z9 and 42 mg of 3-amino-1-ethyl-pyrrolidine were dissolved in 10 mL dichloromethane and stirred with 90 mg of TBTU and 0.5 mL of DIPEA for 12 h at RT. The solvent was eliminated in vacuo, the residue was combined with 10 mL of 10% potassium carbonate solution. The precipitate was suction filtered, washed with water, taken up in dichloromethane, dried and the solvent was eliminated in vacuo. The residue was crystallised from ethyl acetate/petroleum ether. Yield: 24.0 mg.

Example 120

100 mg of the compound Z11 and 73 mg of 4-amino-1 tetrahydro-4H-pyran-4-yl-piperidine were dissolved in 10 mL dichloromethane and stirred with 90 mg of TBTU and 0.5 mL of DIPEA for 1 h at RT. The solvent was eliminated in vacuo, the residue was combined with 10 mL of 10% potassium carbonate solution. The precipitate was suction filtered, washed with water, taken up in dichloromethane, dried and the solvent was eliminated in vacuo. The residue was crystallised from ethyl acetate/petroleum ether. Yield: 89 mg.

Example 212

150 mg of the compound Z5 and 150 mg of trans-4-(4-cyclopropylmethyl-piperazin-1-yl)-cyclohexylamine (as the hydrochloride) were dissolved in 5 mL of dichloromethane and stirred with 160 mg of TBTU and 2 mL of DIPEA for 2 h at RT. The solvent was eliminated in vacuo, the residue was combined with 10 mL of 10% potassium carbonate solution. The precipitate was suction filtered, washed with water, taken up in dichloromethane, and the solvent eliminated in vacuo. The residue was purified over a column (20 mL silica gel, 300 mL ethyl acetate 90/methanol 10+2% conc. ammonia). The appropriate fractions were evaporated down in vacuo and crystallised from ethyl acetate. Yield: 140 mg; m.p. 187° C. (as base).

Example 232

390 mg of the compound Z11 and 240 mg of trans-4-(4-tbutyloxycarbonyl-piperazin-1-yl)-cyclohexylamine were dissolved in 2.5 mL of NMP and stirred with 482 mg of TBTU and 1 mL triethylamine for 2 h at RT. Then 100 mL of water and 200 mg of potassium carbonate were added, the precipitate was suction filtered, washed with water and purified through a silica gel column. The appropriate fractions were evaporated down in vacuo, dissolved in 2 mL dichloromethane, combined with 2 mL of trifluoroacetic acid and stirred for 2 h at RT, combined with another 100 ml of water and 200 mg potassium carbonate and the precipitate was suction filtered and washed with water. Then the precipitate was purified through a silica gel column. The appropriate fractions were evaporated down in vacuo and the residue was crystallised from ethanol and conc. hydrochloric acid. Yield: 95 mg; m.p. 291° C.

Example 213

60 mg of the compound of Example 232 was dissolved in 10 mL ethyl acetate and stirred with 1 mL of acetic anhydride and 1 mL of triethylamine for 30 min. at RT. The solvent was eliminated in vacuo, the residue combined with water and ammonia, the crystals precipitated were suction filtered and washed with water and a little cold acetone. Yield: 40 mg; m.p. 248° C.

Example 218

1.2 g of the compound Z9 and 0.5 g of 1,4-dioxaspiro[4.5]dec-8-ylamine were dissolved in 20 mL dichloromethane and stirred with 1.28 g of TBTU and 4 mL of triethylamine for 12 h at RT. Then 50 mL of water and 0.5 g of potassium carbonate were added, the org. phase was separated off, dried and evaporated down in vacuo. The residue was crystallised from ethyl acetate, combined with 25 mL of 1 N hydrochloric acid and 20 mL of methanol and stirred for 30 min at 50° C.

The methanol was eliminated in vacuo, the precipitate was suction filtered, washed with water and dried.

The residue was taken up in 20 mL dichloromethane, stirred with 0.5 g of thiomorpholine and 0.5 g of NaBH(OAc)$_3$ for 12 h at RT. Then water and potassium carbonate were added, the org. phase was separated off, dried and the solvent was eliminated in vacuo. The residue was purified over a silica gel column. The appropriate fractions were evaporated down in vacuo and the hydrochloride was precipitated with ethereal HCl. Yield: 86 mg of trans-isomer; amorphous powder.

Example 187

200 mg of the compound Z3 in 5 mL dichloromethane was combined with 0.1 mL of diisopropylethylamine and 180 mg of TBTU and stirred for 30 min. Then 191 mg of 4-(4-methyl-piperazin-1-yl)-phenylamine were added and the mixture was stirred overnight. The reaction mixture was combined with water and the aqueous phase extracted with dichloromethane. The combined organic phases were dried over Na$_2$SO$_4$ and Z9 brated down. The residue was purified by column chromatography (eluant: dichloromethane/methanol 100:7).

Yield: 128 mg (light yellow crystals)

The compounds of formula (I) listed in Table 1, inter alia, are obtained analogously to the procedure described hereinbefore. The abbreviations $X_1$, $X_2$, $X_3$, $X_4$ and $X_5$ used in Table 1 in each case denote a link to a position in the general formula shown under Table 1 instead of the corresponding groups $R^1$, $R^2$, $R^3$, $R^4$ and L-$R^5$.

TABLE 1

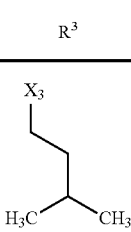

| Example | HELA | H460-VINC | $R^1$ | $R^2$ | Config. $R^1$ or $R^2$ | $R^3$ | $R^4$ | $L_n$—$R^5_m$ | m.p |
|---|---|---|---|---|---|---|---|---|---|
| 1 | 0.046 | 0.604 | H | 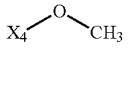 | R | 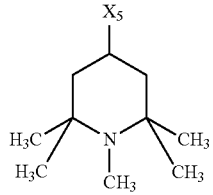 | 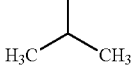 | 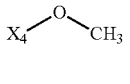 | |
| 2 | 0.056 | 0.971 | H | 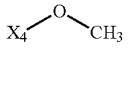 | R | 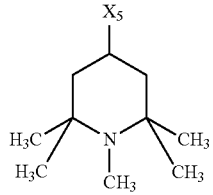 | 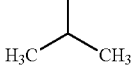 | 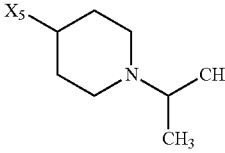 | |
| 3 | 0.061 | | H | 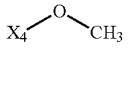 | R | 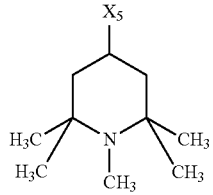 | H | 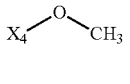 | |

TABLE 1-continued

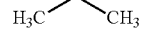

| Example | HELA | H460-VINC | R¹ | R² | Config. R¹ or R² | R³ | R⁴ | $L_n$—$R^5_m$ | m.p |
|---|---|---|---|---|---|---|---|---|---|
| 4 | 0.098 | | H | $X_2$◂CH₃ | R | $X_3$—CH₂CH(CH₃)₂ (isoamyl) | H | $X_5$-(1-ethylpiperidin-4-yl) | |
| 5 | 0.052 | 0.863 | H | $X_2$◂CH₃ | R | $X_3$—CH₂C(CH₃)₃ (neopentyl) | $X_4$—O—CH₃ | $X_5$-(1,2,2,6,6-pentamethylpiperidin-4-yl) | |
| 6 | 0.053 | 0.822 | H | $X_2$◂CH₃ | R | $X_3$—CH₂C(CH₃)₃ | $X_4$—O—CH₃ | $X_5$-(1-ethylpiperidin-4-yl) | |
| 7 | 0.084 | 0.865 | H | $X_2$◂CH₃ | R | $X_3$—CH₂C(CH₃)₃ | $X_4$—O—CH₃ | $X_5$-(1-isopropylpiperidin-4-yl) | |
| 8 | 0.063 | | H | $X_2$◂CH₃ | R | $X_3$—CH₂C(CH₃)₃ | H | $X_5$-(1,2,2,6,6-pentamethylpiperidin-4-yl) | |
| 9 | 0.057 | 0.207 | H | $X_2$◂CH₃ | R | $X_3$—CH₂CH(CH₃)₂ | $X_4$—O—CH₃ | $X_5$-(trans-4-morpholinocyclohexyl) | 253 |

TABLE 1-continued

| Example | HELA | H460-VINC | R¹ | R² | Config. R¹ or R² | R³ | R⁴ | $L_n$—$R^5_m$ | m.p |
|---|---|---|---|---|---|---|---|---|---|
| 10 | 0.091 | | H | X₂◂CH₃ | R | X₃—CH₂—C(CH₃)₃ | H | X₅—(1-benzylpiperidin-4-yl) | |
| 11 | 0.086 | 1.300 | H | X₂◂CH₃ | R | X₃—CH₂—C(CH₃)₃ | H | X₅—(1-ethylpiperidin-4-yl) | |
| 12 | 0.099 | 1.069 | H | X₂◂CH₃ | R | X₃—CH₂—C(CH₃)₃ | H | X₅—(1-isopropylpiperidin-4-yl) | |
| 13 | 0.026 | 1.320 | H | X₂◂CH₃ | R | X₃—cyclopentyl | CH₃—O—X₄ | X₅—(1-isopropylpiperidin-4-yl) | |
| 14 | 0.055 | 3.000 | H | X₂◂CH₃ | R | X₃—cyclopentyl | H | X₅—(1-isopropylpiperidin-4-yl) | |
| 15 | 0.020 | 1.000 | H | X₂◂CH₃ | R | X₃—cyclopentyl | X₄—O—CH₃ | X₅—(4-(pyrrolidin-1-yl)cyclohexyl, trans) | 231 |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 16 | 0.017 | 0.483 | H | X₂⋯CH₃ | R | X₃-cyclopentyl | X₄-O-CH₃ | X₅-trans-cyclohexyl-N-morpholine | 237 |
| 17 | 0.024 | 0.730 | H | X₂⋯CH₃ | R | X₃-cyclopentyl | CH₃-O-X₄ | X₅-piperidinyl-N-CH₂CH₃ | |
| 18 | 0.040 | 1.764 | H | X₂⋯CH₃ | R | X₃-cyclopentyl | H | X₅-piperidinyl-N-CH₂CH₃ | |
| 19 | 0.013 | 0.747 | H | X₂—CH₂CH₃ | R | X₃-cyclopentyl | X₄-O-CH₃ | X₅-trans-cyclohexyl-N-pyrrolidine | 254 |
| 20 | 0.083 | 3.000 | H | X₂⋯CH₃ | R | X₃-CH(CH₃)₂ | CH₃-O-X₄ | X₅-piperidinyl-N-CH₂CH₃ | |

TABLE 1-continued

| Example | HELA | H460-VINC | $R^1$ | $R^2$ | Config. $R^1$ or $R^2$ | $R^3$ | $R^4$ | $L_n$—$R^5_m$ | m.p |
|---|---|---|---|---|---|---|---|---|---|
| 21 | 0.009 | 0.488 | H | X₂—CH₃ | R | X₃-cyclopentyl | CH₃-O-X₄ | X₅-(2,2,6,6-tetramethyl-N-methyl-piperidin-4-yl) | |
| 22 | 0.008 | 0.347 | H | X₂—CH₃ | R | X₃-cyclopentyl | CH₃-O-X₄ | X₅-(1-ethylpiperidin-4-yl) | |
| 23 | 0.013 | 0.679 | H | X₂—CH₃ | R | X₃-cyclopentyl | CH₃-O-X₄ | X₅-(1-isopropylpiperidin-4-yl) | |
| 24 | 0.017 | 0.277 | H | X₂—CH₃ | R | X₃-cyclopentyl | X₄-O-CH₃ | X₅-(trans-4-morpholinocyclohexyl) | 152 |
| 25 | 0.038 | 1.000 | H | X₂—CH₃ | R | X₃-cyclopentyl | X₄-O-CH₃ | X₅-(trans-4-piperidinocyclohexyl) | 254 |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 26 | 0.059 | 0.424 | H | X₂—CH₃ | R | isopropyl (X₃) | X₄—O—CH₃ | X₅-cyclohexyl-N-morpholine | |
| 27 | 0.014 | 0.164 | H | X₂—CH₂CH₃ | R | isopropyl (X₃) | X₄—O—CH₃ | X₅-cyclohexyl-N-morpholine | 292 |
| 28 | 0.018 | 0.160 | H | X₂—CH₂CH₃ | R | isopropyl (X₃) | X₄—O—CH₃ | X₅-cyclohexyl-N-morpholine | 160 |
| 29 | 0.049 | 1.000 | H | X₂—CH₃ | R | isobutyl (X₃—CH₂CH(CH₃)₂) | X₄—O—CH₃ | X₅-cyclohexyl-N-piperidine | 251 |
| 30 | 0.012 | 0.574 | H | X₂—CH₃ | R | cyclopentyl (X₃) | CH₃—O—X₄ | X₅-2,2,6,6-tetramethyl-N-methyl-piperidine | |

TABLE 1-continued
| Example | HELA | H460-VINC | $R^1$ | $R^2$ | Config. $R^1$ or $R^2$ | $R^3$ | $R^4$ | $L_n$—$R^5_m$ | m.p |
|---|---|---|---|---|---|---|---|---|---|
| 31 | 0.023 | 3.000 | H | $X_2$—$CH_3$ | R | 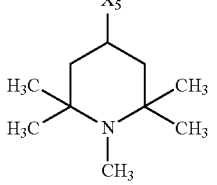 | H | 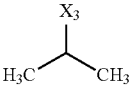 | |
| 32 | 0.049 | 3.000 | H | $X_2$—$CH_3$ | R |  | $X_4$—O—$CH_3$ | 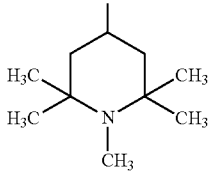 | |
| 33 | 0.097 | 3.000 | H | $X_2$—$CH_3$ | R | 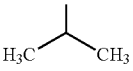 | H | 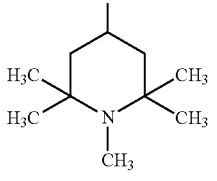 | |
| 34 | 0.055 | 1.000 | H | $X_2$—$CH_3$ | R | 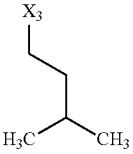 | $X_4$—O—$CH_3$ |  | 242 |
| 35 | 0.088 | 1.000 | H | $X_2$—$CH_3$ | R |  | $X_4$—O—$CH_3$ | 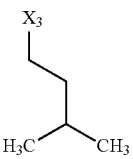 | 213 |

TABLE 1-continued
| Example | HELA | H460-VINC | R¹ | R² | Config. R¹ or R² | R³ | R⁴ | $L_n$—$R^5_m$ | m.p |
|---|---|---|---|---|---|---|---|---|---|
| 36 | 0.021 | 1.000 | H | X₂◂CH₃ | R |  | X₄—O—CH₃ | 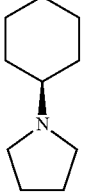 | 232 |
| 37 | 0.072 | 0.762 | H | X₂◂CH₃ | R | 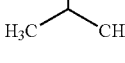 | X₄—O—CH₃ |  | 160 |
| 38 | 0.087 | 0.278 | H | X₂◂CH₃ | R | 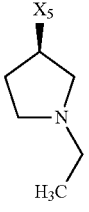 | X₄—O—CH₃ | 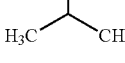 | 225 |
| 39 | 0.075 | 1.000 | H | X₂◂CH₃ | R |  | H | 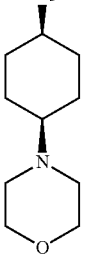 | |
| 40 | 0.038 | 0.187 | H | X₂◂CH₃ | R |  | X₄—O—CH₃ | 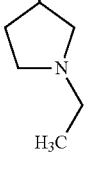 | 226 |

TABLE 1-continued

| Example | HELA | H460-VINC | $R^1$ | $R^2$ | Config. $R^1$ or $R^2$ | $R^3$ | $R^4$ | $L_n$—$R^5{}_m$ | m.p |
|---|---|---|---|---|---|---|---|---|---|
| 41 | 0.083 | 3.000 | H | $X_2$—CH$_3$ | R | phenyl-$X_3$ | CH$_3$—O—$X_4$ | 1-methylpiperidin-4-yl-$X_5$ | |
| 42 | 0.076 | 2.310 | H | $X_2$—CH$_2$CH$_3$ | R | isobutyl-$X_3$ | CH$_3$—O—$X_4$ | 8-methyl-8-azabicyclo[3.2.1]oct-3-yl-$X_5$ | |
| 43 | 0.094 | 3.000 | $X_1$—CH$_3$ | $X_2$—CH$_3$ | | isobutyl-$X_3$ | H$_3$C—O—$X_4$ | 8-methyl-8-azabicyclo[3.2.1]oct-3-yl-$X_5$ | 218 |
| 44 | 0.009 | 0.204 | H | $X_2$—CH$_2$CH$_3$ | R | cyclopentyl-$X_3$ | H | 1-methylpiperidin-4-yl-$X_5$ | |
| 45 | 0.022 | 0.792 | H | $X_2$—CH$_2$CH$_3$ | R | cyclopentyl-$X_3$ | H$_3$C—O—$X_4$ | 8-methyl-8-azabicyclo[3.2.1]oct-3-yl-$X_5$ | |
| 46 | 0.012 | 0.208 | H | $X_2$—CH$_2$CH$_3$ | R | cyclopentyl-$X_3$ | H$_3$C—O—$X_4$ | 1-methylpiperidin-4-yl-$X_5$ | 203 |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 47 | 0.028 | | H | X₂—CH₃ | R | cyclopentyl-X₃ | H | N-methyl-8-azabicyclic-X₅ | |
| 48 | 0.083 | 3.000 | H | X₂—CH₃ | R | phenyl-X₃ | H | 1-methylpiperidin-4-yl-X₅ | |
| 49 | 0.059 | 0.529 | H | X₂—CH₃ | R | cyclopentyl-X₃ | CH₃—O—X₄ | 2-methyl-2-(pyrrolidin-1-ylmethyl)propyl-X₅ | |
| 50 | 0.081 | 0.436 | H | X₂—CH₃ | R | neopentyl-X₃ | X₄—O—CH₃ | 2-methyl-2-(pyrrolidin-1-ylmethyl)propyl-X₅ | |
| 51 | 0.080 | 0.150 | H | X₂-cyclopropyl | R | cyclopentyl-X₃ | CH₃—O—X₄ | 2,2-dimethyl-3-(dimethylamino)propyl-X₅ | |
| 52 | 0.079 | 0.153 | H | X₂—CH₃ | R | neopentyl-X₃ | CH₃—O—X₄ | 2,2-dimethyl-3-(dimethylamino)propyl-X₅ | |

TABLE 1-continued

| Example | HELA | H460-VINC | R¹ | R² | Config. R¹ or R² | R³ | R⁴ | $L_n$—$R^5_m$ | m.p |
|---|---|---|---|---|---|---|---|---|---|
| 53 | 0.076 | 0.245 | X₁—CH₃ | X₂—CH₃ |  | isopentyl (X₃—CH₂CH₂CH(CH₃)₂) | CH₃—O—X₄ | X₅—C(CH₃)₂—CH₂—N(CH₃)₂ |  |
| 54 | 0.031 | 0.226 | H | X₂—CH₂CH₃ | R | isobutyl (X₃—CH(CH₃)₂) | CH₃—O—X₄ | X₅—C(CH₃)₂—CH₂—pyrrolidinyl |  |
| 55 | 0.013 | 0.086 | H | X₂—CH₂CH₃ | R | cyclopentyl (X₃) | CH₃—O—X₄ | X₅—C(CH₃)₂—CH₂—pyrrolidinyl |  |
| 56 | 0.064 | 0.324 | H | X₂—CH₃ | R | isobutyl | CH₃—O—X₄ | X₅—C(CH₃)₂—CH₂—pyrrolidinyl |  |
| 57 | 0.038 | 0.067 | H | X₂—CH₂CH₃ | R | isobutyl | CH₃—O—X₄ | X₅—C(CH₃)₂—CH₂—N(CH₃)₂ |  |
| 58 | 0.010 | 0.023 | H | X₂—CH₂CH₃ | R | cyclopentyl (X₃) | CH₃—O—X₄ | X₅—C(CH₃)₂—CH₂—N(CH₃)₂ |  |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 59 | 0.095 | 1.000 | H | X₂◂CH₃ | R | phenyl | H₃C—O—X₄ | 1-methylpiperidin-4-yl (X₅) | |
| 60 | 0.041 | 0.189 | H | X₂◂CH₃ | R | cyclopentyl | CH₃—O—X₄ | (CH₃)₂C(CH₃)CH₂N(CH₃)₂ with X₅ | |
| 61 | 0.065 | 1.040 | X₁—CH₃ | X₂◂CH₃ | | isobutyl (X₃) | H₃C—O—X₄ | 1-methylpiperidin-4-yl (X₅) | 217 |
| 62 | 0.058 | 0.538 | H | X₂◂CH₃ | R | cyclopentyl | CH₃—O—X₄ | (H₃C—CH₂)₂N—CH₂—X₅ | 259 |
| 63 | 0.081 | 0.206 | H | X₂◂CH₃ | R | cyclopentyl | CH₃—O—X₄ | morpholino-propyl-X₅ | 184 |
| 64 | 0.064 | 0.894 | H | X₂◂CH₃ | R | cyclopentyl | CH₃—O—X₄ | piperidino-propyl-X₅ | 175 |
| 65 | 0.052 | 0.216 | H | X₂◂CH₃ | R | cyclopentyl | CH₃—O—X₄ | morpholino-ethyl-X₅ | 172 |
| 66 | 0.064 | 0.250 | H | X₂◂CH₃ | R | cyclopentyl | CH₃—O—X₄ | piperidino-ethyl-X₅ | 164 |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 67 | 0.052 | 0.566 | H | X₂—CH₃ (wedge) | R | cyclopentyl-X₃ | CH₃—O—X₄ | (CH₃)(H₃C)N—CH₂CH₂—X₅ | 115 |
| 68 | 0.092 | 1.242 | H | X₂—CH₃ (wedge) | R | cyclopentyl-X₃ | H | H₃C—N-bicyclic—X₅ | |
| 69 | 0.055 | 0.633 | H | X₂—CH₃ (wedge) | R | cyclopentyl-X₃ | H | morpholino-(CH₂)₃—X₅ | |
| 70 | 0.092 | 1.000 | H | X₂—CH₃ (wedge) | R | cyclopentyl-X₃ | H | piperidino-CH₂CH₂—X₅ | |
| 71 | 0.035 | 0.227 | H | X₂—CH₃ | R | isopropyl-X₃ | CH₃—O—X₄ | X₅—CH₂CH₂—morpholino | 146 |
| 72 | 0.050 | | H | X₂—CH₃ | R | isopropyl-X₃ | CH₃—O—X₄ | X₅—CH₂CH₂—piperidino | |
| 73 | 0.091 | | H | X₂—CH₃ | R | isopropyl-X₃ | H | X₅—CH₂CH₂—N(CH₂CH₃)₂ | |
| 74 | 0.043 | | H | X₂—CH₃ | R | isopropyl-X₃ | CH₃—O—X₄ | X₅—CH₂CH₂—N(CH₂CH₃)₂ | |

TABLE 1-continued
| Example | HELA | H460-VINC | R¹ | R² | Config. R¹ or R² | R³ | R⁴ | Lₙ—R⁵ₘ | m.p |
|---|---|---|---|---|---|---|---|---|---|
| 75 | 0.046 | 0.557 | H | 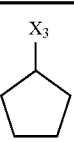 | R | 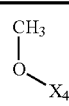 | 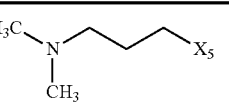 |  | |
| 76 | 0.068 | | H | 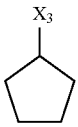 | R | 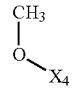 | 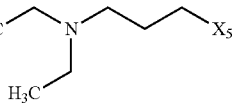 |  | |
| 77 | 0.055 | 1.000 | H | 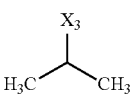 | R | 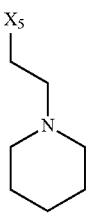 | H |  | |
| 78 | 0.035 | 0.610 | H | 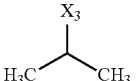 | R | 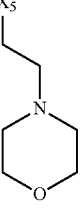 | H |  | |
| 79 | 0.043 | | H | 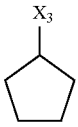 | R | 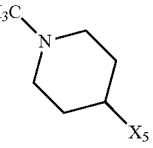 | H |  | |
| 80 | 0.038 | 0.286 | H | 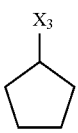 | R | 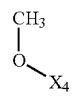 | 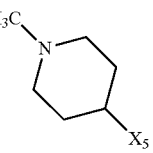 |  | |
| 81 | 0.050 | 0.237 | H | 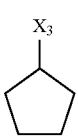 | R | 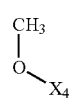 | 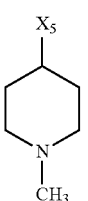 | | 194 |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 82 | 0.083 | 1.580 | H | X₂-cyclopropyl | R | X₃-cyclopentyl | CH₃-O-X₄ | X₅-(N-methyl azabicyclic) | |
| 83 | 0.069 | 0.263 | H | X₂–CH₃ | R | X₃-cyclopentyl | H₃C-X₄ | H₃C-N-piperidinyl-X₅ | |
| 84 | 0.015 | 0.312 | H | X₂–CH₃ | R | X₃-cyclohexyl | CH₃-O-X₄ | X₅-(N-methyl piperidinyl) | |
| 85 | 0.025 | 0.754 | H | X₂–CH₃ | R | X₃-cyclohexyl | H | X₅-(N-methyl piperidinyl) | |
| 86 | 0.038 | 0.024 | H | X₂–CH₃ | R | X₃-cyclohexyl | CH₃-O-X₄ | X₅-C(CH₃)₂-CH₂-N(CH₃)₂ | |
| 87 | 0.029 | 0.066 | H | X₂–CH₃ | R | X₃-cyclohexyl | CH₃-O-X₄ | X₅-C(CH₃)₂-CH₂-pyrrolidinyl | |

TABLE 1-continued
| Example | HELA | H460-VINC | R¹ | R² | Config. R¹ or R² | R³ | R⁴ | $L_n$—$R^5_m$ | m.p |
|---|---|---|---|---|---|---|---|---|---|
| 88 | 0.020 | 1.018 | H | 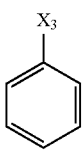 | R | 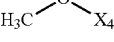 | 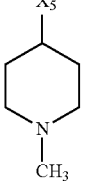 |  | |
| 89 | 0.047 | 0.245 | H | 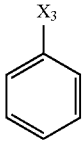 | R | 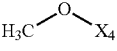 | 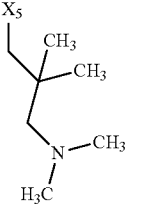 |  | |
| 90 | 0.032 | 0.137 | H | 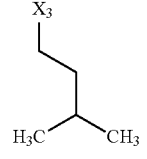 | R |  | 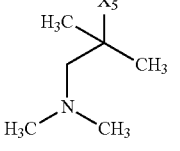 |  | |
| 91 | 0.041 | 1.780 | H | 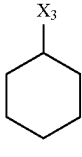 | R |  | 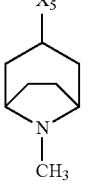 |  | |
| 92 | 0.043 | | H | 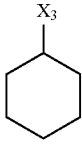 | R | 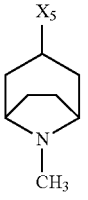 | H |  | 181 |
| 93 | 0.060 | | H | 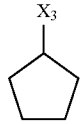 | R | 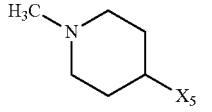 | H | | |

TABLE 1-continued

| Ex-am-ple | HELA | H460-VINC | R¹ | R² | Config. R¹ or R² | R³ | R⁴ | Lₙ—R⁵ₘ | m.p |
|---|---|---|---|---|---|---|---|---|---|
| 94 | 0.018 | 0.510 | H | X₂▬CH₃ | R | X₃-cyclohexyl | H₃C-X₄ | X₅-(N-methylpiperidin-4-yl) | 178 |
| 95 | 0.047 | 1.000 | H | X₂▬CH₃ | R | X₃-cyclohexyl | H₃C-X₄ | X₅-(N-methyl-8-azabicyclo) | |
| 96 | 0.011 | 0.577 | H | X₂—CH₃ | R | X₃-cyclohexyl | H₃C-O-X₄ | X₅-(N-methylpiperidin-4-yl) | 203 |
| 97 | 0.032 | 0.066 | H | X₂—CH₃ | R | X₃-cyclohexyl | H₃C-O-X₄ | X₅-(trans-4-morpholinocyclohexyl) | 179 |
| 98 | 0.077 | 1.319 | H | X₂▬CH₃ | R | X₃-cyclohexyl | X₄-O-CH₃ | X₅-(trans-4-pyrrolidinylcyclohexyl) | |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 99 | 0.025 | 0.209 | H | X₂—CH₂CH₃ | R | X₃—CH(CH₃)₂ | X₄—O—CH₃ | X₅—(trans-cyclohexyl)—N(piperazine)N—CH₂-cyclopropyl | 280 |
| 100 | 0.058 | 0.124 | H | X₂—CH₃ | R | X₃—CH₂CH(CH₃)₂ | X₄—O—CH₃ | X₅—(trans-cyclohexyl)—N(piperazine)N—CH₂-cyclopropyl | 233 |
| 101 | 0.031 | 0.124 | H | X₂—CH₃ | R | X₃—CH(CH₃)₂ | CH₃—O—X₄ | X₅—(piperidin-4-yl)—N—CH₂-phenyl | |
| 102 | 0.006 | 0.053 | H | X₂—CH₂CH₃ | R | X₃—CH(CH₃)₂ | CH₃—O—X₄ | X₅—(piperidin-4-yl)—N—CH₂-phenyl | |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 103 | 0.005 | 0.076 | H | X₂⬛CH₃ | R | cyclopentyl-X₃ | CH₃O—X₄ | 4-(N-benzyl)piperidinyl-X₅ | |
| 104 | 0.041 | 0.133 | H | X₂⬛CH₃ | R | phenyl-X₃ | CH₃O—X₄ | 4-(N-benzyl)piperidinyl-X₅ | |
| 105 | 0.015 | 0.055 | H | X₂⬛CH₃ | R | cyclopentyl-X₃ | X₄O—CH₃ | trans-4-[4-(cyclopropylmethyl)piperazin-1-yl]cyclohexyl-X₅ | 229 |
| 106 | 0.025 | 1.000 | H | X₂⬛CH₃ | R | cyclopentyl-X₃ | X₄O—CH₃ | trans-4-(4-methylpiperazin-1-yl)cyclohexyl-X₅ | 213 |

TABLE 1-continued
| Example | HELA | H460-VINC | R¹ | R² | Config. R¹ or R² | R³ | R⁴ | $L_n$—$R^5_m$ | m.p |
|---|---|---|---|---|---|---|---|---|---|
| 107 | 0.043 | 0.363 | H |  | R | 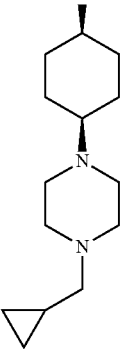 | 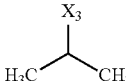 |  | 285 |
| 108 | 0.016 | 1.000 | H | 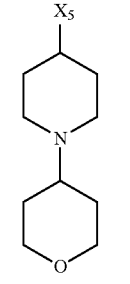 | R |  |  | 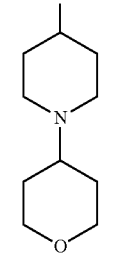 | |
| 109 | 0.031 | 0.760 | H | 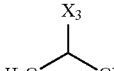 | R | |  | | |
| 110 | 0.027 | 0.122 | H | | R | | | 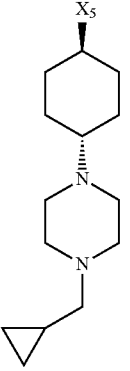 | 278 |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 111 | 0.023 | 0.503 | H | X₂–CH₃ | R | X₃–CH₂CH(CH₃)₂ | CH₃O–X₄ | X₅–piperidinyl–tetrahydropyranyl | |
| 112 | 0.075 | 0.345 | H | X₂–CH₃ | R | X₃–CH(CH₃)₂ | X₄–OCH₃ | X₅–cyclohexyl–piperazinyl–CH₂–cyclopropyl | 264 |
| 113 | 0.037 | 0.687 | H | X₂–CH₂CH₃ | R | X₃–CH(CH₃)₂ | X₄–OCH₃ | X₅–cyclohexyl–piperazinyl–CH₃ | 279 |
| 114 | 0.064 | 0.766 | H | X₂–CH₃ | R | X₃–CH₂CH(CH₃)₂ | X₄–OCH₃ | X₅–cyclohexyl–N(CH₃)₂ | 234 |

TABLE 1-continued

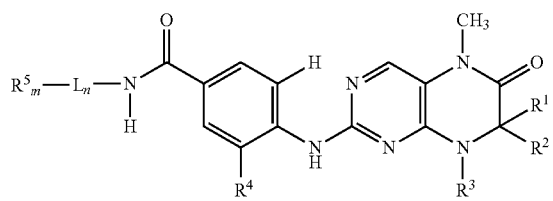

| Example | HELA | H460-VINC | R¹ | R² | Config. R¹ or R² | R³ | R⁴ | Lₙ—R⁵ₘ | m.p |
|---|---|---|---|---|---|---|---|---|---|
| 115 | 0.016 | 0.076 | H | X₂⟵CH₃ | R | cyclohexyl-X₃ | CH₃-O-X₄ | 4-(1-benzylpiperidinyl)-X₅ | |
| 116 | 0.006 | 0.174 | H | X₂—CH₃ (ethyl) | R | cyclopentyl-X₃ | CH₃-O-X₄ | 1-(tetrahydropyran-4-yl)piperidin-4-yl-X₅ | |
| 117 | 0.010 | 0.370 | H | X₂⟵CH₃ | R | cyclohexyl-X₃ | CH₃-O-X₄ | 1,2,2,6,6-pentamethylpiperidin-4-yl-X₅ | |
| 118 | 0.010 | 0.279 | H | X₂⟵CH₃ | R | cyclohexyl-X₃ | CH₃-O-X₄ | 1-isopropylpiperidin-4-yl-X₅ | |
| 119 | 0.008 | 0.438 | H | X₂⟵CH₃ | R | cyclohexyl-X₃ | CH₃-O-X₄ | 1-ethylpiperidin-4-yl-X₅ | |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 120 | 0.014 | 0.374 | H | X₂◂CH₃ | R | cyclohexyl-X₃ | CH₃-O-X₄ | 4-(tetrahydropyran-4-yl)piperidin-1-yl-X₅ | 154 |
| 121 | 0.011 | 0.427 | H | X₂◂CH₃ | R | cyclohexyl-X₃ | CH₃-O-X₄ | (3S)-1-ethylpyrrolidin-3-yl-X₅ | |
| 122 | 0.009 | 0.261 | H | X₂◂CH₃ | R | cyclohexyl-X₃ | CH₃-O-X₄ | (3S)-1-isopropylpyrrolidin-3-yl-X₅ | |
| 123 | 0.043 | 0.490 | H | X₂◂CH₃ | R | cyclohexyl-X₃ | CH₃-O-X₄ | (3R)-1-ethylpyrrolidin-3-yl-X₅ | |
| 124 | 0.006 | 0.391 | H | X₂◂CH₃ | R | cyclohexyl-X₃ | CH₃-O-X₄ | (3R)-1-isopropylpyrrolidin-3-yl-X₅ | |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 125 | 0.049 | 0.795 | H | X₂▸CH₃ | R | X₃-cyclohexyl | X₄-O-CH₃ | X₅-cyclohexyl-N-pyrrolidinyl | 283 |
| 126 | 0.051 | 0.742 | H | X₂▸CH₃ | R | X₃-cyclohexyl | X₄-O-CH₃ | X₅-cyclohexyl-N-piperidinyl | 238 |
| 127 | 0.045 | 0.787 | H | X₂▸CH₃ | R | X₃-cyclohexyl | X₄-O-CH₃ | X₅-cyclohexyl-N-piperidinyl | 221 |
| 128 | 0.015 | 0.282 | H | X₂-CH₂CH₃ | R | X₃-cyclopentyl | X₄-O-CH₃ | X₅-cyclohexyl-N-piperidinyl | 257 |

TABLE 1-continued
| Example | HELA | H460-VINC | R¹ | R² | Config. R¹ or R² | R³ | R⁴ | Lₙ—R⁵ₘ | m.p |
|---|---|---|---|---|---|---|---|---|---|
| 129 | 0.035 | 0.646 | H | 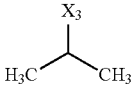 | R |  | 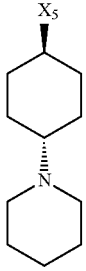 |  | 284 |
| 130 | 0.015 | 0.091 | H | 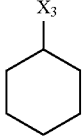 | R |  | 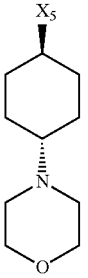 |  | 236 |
| 131 | 0.023 | 0.101 | H | 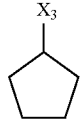 | R |  | 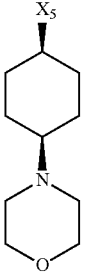 |  | 141 |
| 132 | 0.062 | 1.000 | H | 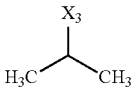 | R |  | 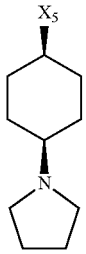 | | 268 |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 133 | 0.011 | 0.075 | H | X₂—CH₃ (ethyl) | R | X₃-cyclopentyl | X₄—O—CH₃ | X₅-cyclohexyl-N-morpholine | 272 |
| 134 | 0.015 | 0.063 | H | X₂—CH₃ (ethyl) | R | X₃-cyclopentyl | X₄—O—CH₃ | X₅-cyclohexyl-N-piperazine-N-phenyl | 319 |
| 135 | 0.012 | 0.699 | H | X₂—CH₃ (ethyl) | R | X₃-isopropyl | X₄—O—CH₃ | X₅-cyclohexyl-N-pyrrolidine | 289 |
| 136 | 0.041 | 0.821 | H | X₂—CH₃ (ethyl) | R | X₃-cyclopentyl | X₄—O—CH₃ | X₅-cyclohexyl-N-piperidine | 201 |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 137 | 0.039 | 0.148 | H | X₂―CH₃ (wedge) | R | X₃-cyclohexyl | X₄-OCH₃ | X₅-cyclohexyl-morpholine | 223 |
| 138 | 0.043 | 1.137 | H | X₂―CH₃ | R | X₃-cyclopentyl | X₄-OCH₃ | X₅-cyclohexyl-pyrrolidine | 217 |
| 139 | 0.097 | 3.000 | H | X₂―CH₃ | R | X₃-isopropyl | H₃C-O-CH₃ | X₅-N-methyl bicyclic amine | 112 |
| 140 | 0.029 | 1.970 | H | X₂―CH₃ | R | X₃-isopropyl | H₃C-O-CH₃ | X₅-N-methylpiperidine | 215 |
| 141 | 0.057 | | H | X₂―CH₃ | R | X₃-isopropyl | H₃C-O-CH₃ | X₅-propyl-morpholine | 198 |

TABLE 1-continued
| Example | HELA | H460-VINC | R¹ | R² | Config. R¹ or R² | R³ | R⁴ | $L_n-R^5{}_m$ | m.p |
|---|---|---|---|---|---|---|---|---|---|
| 142 | 0.030 | | H | 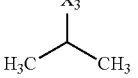 | R | 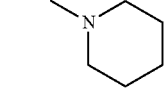 |  | 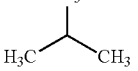 | 192 |
| 143 | 0.086 | | H | 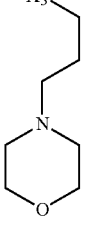 | R |  | H | 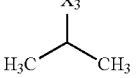 | 139 |
| 144 | 0.044 | | H | 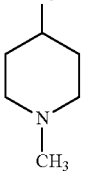 | R |  | H | 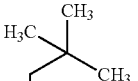 | 191 |
| 145 | 0.043 | 3.000 | H | 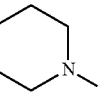 | R |  | 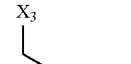 | 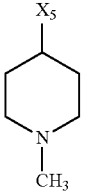 | |
| 146 | 0.066 | 0.966 | H |  | R | 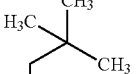 |  | 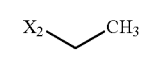 | |
| 147 | 0.055 | 1.760 | H | H₃C—X₂ | R | | H | 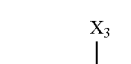 | |
| 148 | 0.087 | | H | X₂—CH₃ | R | X₃ (isopentyl) | CH₃—O—X₄ | 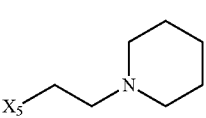 | |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 149 | 0.085 | | H | X₂–CH₂CH₃ | R | X₃–CH₂CH₂–CH(CH₃)CH₃ | CH₃–O–X₄ | X₅–CH₂CH₂–N(CH₂CH₃)₂ | |
| 150 | 0.043 | | H | X₂–CH₂CH₃ | R | X₃–CH₂CH₂–CH(CH₃)CH₃ | H | X₅–CH₂CH₂–piperidine | |
| 151 | 0.043 | | H | X₂–CH₂CH₃ | R | X₃–CH₂CH₂–CH(CH₃)CH₃ | CH₃–O–X₄ | X₅–(CH₂)₃–morpholine | 155 |
| 152 | 0.081 | | H | X₂–CH₂CH₃ | R | X₃–CH₂CH₂–CH(CH₃)CH₃ | CH₃–O–X₄ | X₅–(CH₂)₃–N-methylpiperazine | 147 |
| 153 | 0.072 | 2.640 | H | X₂–CH₂CH₃ | R | X₃–CH₂CH₂–CH(CH₃)CH₃ | CH₃–O–X₄ | X₅–(CH₂)₄–N(CH₂CH₃)₂ | 128 |
| 154 | 0.097 | | H | X₂–CH₂CH₃ | R | X₃–CH₂CH₂–CH(CH₃)CH₃ | H | X₅–(CH₂)₃–N-methylpiperazine | |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 155 | 0.079 | | H | X₂—CH₂—CH₃ | R | X₃—CH₂CH₂CH(CH₃)₂ | H | X₅—(CH₂)₃—morpholine | |
| 156 | 0.048 | 0.481 | H | X₂—CH₂—CH₃ | R | X₃—CH₂CH₂CH(CH₃)₂ | CH₃O—X₄ | X₅—(CH₂)₂—morpholine | 173 |
| 157 | 0.051 | | H | X₂—CH₂—CH₃ | R | X₃—CH₂CH₂CH(CH₃)₂ | CH₃O—X₄ | X₅—(CH₂)₃—pyrrolidine | 134 |
| 158 | 0.043 | 0.536 | H | X₂—CH₂—CH₃ | R | X₃—CH₂CH₂CH(CH₃)₂ | CH₃O—X₄ | X₅—(CH₂)₂—N(CH₂CH₃)₂ | 230 |
| 159 | 0.029 | 1.000 | H | X₂—CH₂—CH₃ | R | X₃—CH₂CH₂CH(CH₃)₂ | CH₃O—X₄ | X₅—(CH₂)₂—N(CH₃)₂ | 260 |
| 160 | 0.037 | 0.728 | H | X₂—CH₂—CH₃ | R | X₃—CH₂CH₂CH(CH₃)₂ | CH₃O—X₄ | X₅—(CH₂)₂—N(CH(CH₃)₂)₂ | 193 |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 161 | 0.081 | | X₁—CH₃ | X₂—CH₃ | | X₃—CH₂CH(CH₃)₂ (isobutyl on X₃) | H₃C—O—X₄ | X₅—CH₂CH₂—N(CH₂CH₃)₂ | 199 |
| 162 | 0.071 | 0.903 | X₁—CH₃ | X₂—CH₃ | | X₃—CH₂CH(CH₃)₂ | H₃C—O—X₄ | X₅—(N-methylpiperidin-4-yl) | 254 |
| 163 | 0.071 | 1.000 | H | X₂—CH₂CH₃ | R | X₃—CH₂CH(CH₃)₂ | CH₃—O—X₄ | X₅—(quinuclidin-3-yl) | 249 |
| 164 | 0.030 | 0.975 | H | X₂—CH₂CH₃ | R | X₃—CH₂CH(CH₃)₂ | CH₃—O—X₄ | X₅—(CH₂)₃N(CH₃)₂ | |
| 165 | 0.046 | 0.668 | H | X₂—CH₂CH₃ | R | X₃—CH₂CH(CH₃)₂ | CH₃—O—X₄ | X₅—(CH₂)₃N(CH₂CH₃)₂ | |
| 166 | | | H | X₂—CH₂CH₃ | R | X₃—cyclopentyl | CH₃—O—X₄ | X₅—(4-(morpholinomethyl)phenyl) | |

TABLE 1-continued

| Example | HELA | H460-VINC | R¹ | R² | Config. R¹ or R² | R³ | R⁴ | $L_n$—$R^5_m$ | m.p |
|---|---|---|---|---|---|---|---|---|---|
| 167 | 0.034 | 0.817 | H | X₂—CH₃ (ethyl) | R | X₃-CH₂CH(CH₃)CH₂CH₃ (isopentyl) | CH₃-O-X₄ | X₅-CH₂CH₂-(1-methylpyrrolidin-2-yl) | |
| 168 | 0.042 | 0.088 | H | X₂—CH₃ | R | isopentyl | CH₃-O-X₄ | X₅-CH₂-C(CH₃)₂-CH₂-N(CH₃)₂ | |
| 169 | 0.044 | 0.503 | H | X₂—CH₃ | R | isopentyl | CH₃-O-X₄ | X₅-(CH₂)₃-piperidin-1-yl | |
| 170 | 0.045 | 0.427 | H | X₂—CH₃ | R | isopentyl | CH₃-O-X₄ | X₅-CH₂CH₂-pyrrolidin-1-yl | 170 |
| 171 | 0.031 | 0.790 | H | X₂—CH₃ | R | isopentyl | CH₃-O-X₄ | X₅-(1-methylpiperidin-4-yl) | 196 |
| 172 | 0.020 | 0.772 | H | X₂—CH₃ | R | isopentyl | CH₃-O-X₄ | X₅-(1-methylazepan-4-yl) | 166 |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 173 | 0.070 | 0.871 | H | X₂–CH₃ (ethyl) | R | X₃–CH₂CH(CH₃)CH₃ (isopentyl) | CH₃–O–X₄ | N-methyl azabicyclic (X₅) | |
| 174 | 0.000 | 0.155 | H | X₂–CH₂CH₃ | R | X₃–CH₂CH(CH₃)CH₃ | CH₃–O–X₄ | 1-benzylpiperidin-4-yl (X₅) | |
| 175 | 0.000 | 0.296 | H | X₂◂CH₃ | R | X₃-cyclopentyl | CH₃–O–X₄ | (CH₃)₂C(CH₂N(CH₃)₂)–X₅ | |
| 176 | 0.000 | 0.301 | H | X₂–CH₂CH₃ | R | X₃–CH(CH₃)₂ | CH₃–O–X₄ | (CH₃)₂C(CH₂N(CH₃)₂)–X₅ | |
| 177 | 0.000 | 0.082 | H | X₂–CH₂CH₃ | R | X₃-cyclopentyl | CH₃–O–X₄ | (CH₃)₂C(CH₂N(CH₃)₂)–X₅ | |
| 178 | 0.000 | 1.000 | H | X₂–CH₂CH₃ | R | X₃–CH(CH₃)₂ | CH₃–O–X₄ | piperidin-4-yl (X₅) | |
| 179 | 0.000 | 1.000 | H | X₂–CH₂CH₃ | R | X₃–CH₂CH(CH₃)CH₃ | CH₃–O–X₄ | piperidin-4-yl (X₅) | |

TABLE 1-continued

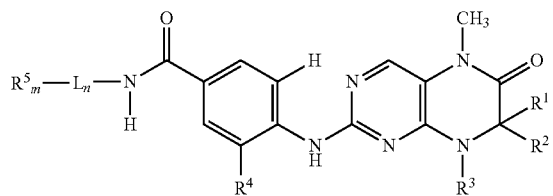

| Example | HELA | H460-VINC | R¹ | R² | Config. R¹ or R² | R³ | R⁴ | $L_n$—$R^5_m$ | m.p |
|---|---|---|---|---|---|---|---|---|---|
| 180 | 0.000 | 0.147 | H | X₂—CH₃ | R | X₃-cyclohexyl | H₃C—O—X₄ | X₅-(4-piperidinyl)-N-benzyl | 136 |
| 181 | 0.000 | 0.754 | H | X₂◂CH₃ | R | X₃-tetrahydropyran-4-yl | CH₃—O—X₄ | X₅-(4-piperidinyl)-N-benzyl | |
| 182 | | | H | X₂◂CH₃ | R | X₃-cyclopentyl | CH₃—O—X₄ | X₅-C(CH₃)₂-CH₂-morpholine | |
| 183 | | | H | X₂—CH₃ | R | X₃-CH(CH₃)₂ isopropyl | CH₃—O—X₄ | X₅-C(CH₃)₂-CH₂-morpholine | |
| 184 | | | H | X₂—CH₃ | R | X₃-cyclopentyl | CH₃—O—X₄ | X₅-C(CH₃)₂-CH₂-morpholine | |

TABLE 1-continued

| Example | HELA | H460-VINC | R[1] | R[2] | Config. R[1] or R[2] | R[3] | R[4] | $L_n$—$R^5_m$ | m.p |
|---|---|---|---|---|---|---|---|---|---|
| 185 | | H | H | X₂—CH₃ (wedge) | R | 4-methoxyphenyl-X₃ | CH₃-O-X₄ | neopentyl-morpholino-X₅ | 217 |
| 186 | | H | H | X₂—CH₃ (wedge) | R | cyclohexyl-X₃ | CH₃-O-X₄ | 4-(4-methylpiperazin-1-yl)phenyl-X₅ | 287 |
| 187 | | H | H | X₂—CH₃ | R | cyclopentyl-X₃ | CH₃-O-X₄ | 4-(4-methylpiperazin-1-yl)phenyl-X₅ | 223 |
| 188 | | H | H | X₂—CH₃ (wedge) | R | cyclopentyl-X₃ | Cl-X₄ | 1-methylpiperidin-4-yl-X₅ | 161 |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 189 | | | H | X₂—CH₃ | R | X₃—cyclohexyl | X₄—O—CH₃ | X₅—trans-cyclohexyl-N-morpholine | 267 |
| 190 | | | H | X₂◂CH₃ | R | X₃—cyclopentyl | CH₃—O—X₄ | X₅—piperidine | |
| 191 | | | H | X₂—cyclopropyl | R | X₃—CH(CH₃)₂ | H₃C—CH₂—O—X₄ | X₅—N-methylpiperidine | |
| 192 | | | H | X₂◂CH₃ | R | X₃—cyclohexyl | CH₃—O—X₄ | X₅—C(CH₃)₂—CH₂—morpholine | |
| 193 | | | H | X₂—CH₃ | R | X₃—cyclohexyl | CH₃—O—X₄ | X₅—C(CH₃)₂—CH₂—morpholine | |
| 194 | | | H | X₂—CH₃ | R | X₃—phenyl | CH₃—O—X₄ | X₅—C(CH₃)₂—CH₂—morpholine | |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 195 | | H | | X₂—CH₃ | R | X₃—CH(CH₃)—CH(CH₃)₂ (isobutyl) | CH₃—O—X₄ | H₃C-C(CH₃)₂-CH₂-N(morpholine), X₅ | |
| 196 | | H | | X₂—CH₂CH₃ | R | X₃—CH₂CH(CH₃)CH₃ (isoamyl) | CH₃—O—X₄ | H₃C-C(CH₃)₂-CH₂-N(N-methylpiperazine), X₅ | |
| 197 | | H | | X₂—(cyclopropyl) | | X₃—CH₂CH(CH₃)CH₃ | CH₃—O—X₄ | H₃C-C(CH₃)₂-CH₂-N(N-methylpiperazine), X₅ | |
| 198 | | H | | X₂, X₃ (cyclopentane fused) | R | | H₃C—O—X₄ | X₅-(1-methylpiperidin-4-yl) | 301 |
| 199 | | H | | X₂, X₃ (cyclopentane fused) | R | | H₃C—O—X₄ | X₅-(trans-4-morpholinocyclohexyl) | 291 |

TABLE 1-continued
| Example | HELA | H460-VINC | R¹ | R² | Config. R¹ or R² | R³ | R⁴ | $L_n$—$R^5_m$ | m.p |
|---|---|---|---|---|---|---|---|---|---|
| 200 | | | H |  | R | | 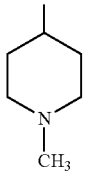 |  | |
| 201 | | | H | 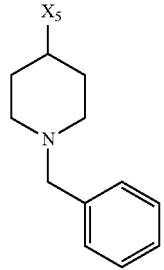 | R | |  |  | |
| 202 | | | X₁—CH₃ | X₂—CH₃ | | 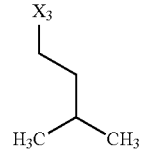 | 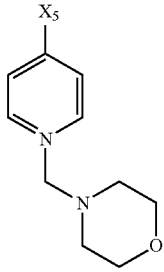 |  | |
| 203 | | | H | X₂▲CH₃ | R | 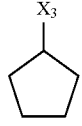 | Cl—X₄ | 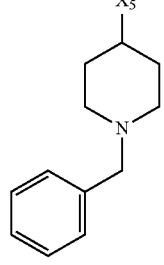 | |
| 204 | | | H | X₂▲CH₃ | R |  | 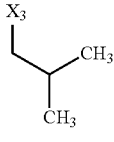 | 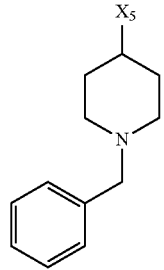 | |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 205 | | | H | X₂—CH₃ | R | X₃—CH(CH₃)₂ (isobutyl) | X₄—O—CH₃ | X₅-cyclohexyl-morpholine | 255 |
| 206 | | | H | X₂—CH₃ | R | X₃—C(CH₃)₃CH₃ (neopentyl) | X₄—O—CH₃ | X₅-cyclohexyl-piperazine-CH₂-cyclopropyl | 190 |
| 207 | | | H | X₂—CH₃ | R | X₃—C(CH₃)₃CH₃ (neopentyl) | X₄—O—CH₃ | X₅-cyclohexyl-morpholine | 236 |
| 208 | | | H | X₂—CH₃ | R | X₃—C(CH₃)₃CH₃ (neopentyl) | X₄—O—CH₃ | X₅-cyclohexyl-piperazine-CH₂-cyclopropyl | 192 |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 209 | | | H | X₂—CH₃ (wedge) | R | X₃—CH(CH₃)₂ (isobutyl) | X₄—O—CH₃ | X₅-cyclohexyl-N-piperazine-N-CH₃ | 211 |
| 210 | | | H | X₂—CH₃ (wedge) | R | X₃—cyclopentyl | X₄—O—CH₃ | X₅-cyclohexyl-N-piperazine-N-CH₃ | 210 |
| 211 | | | X₁—CH₃ | X₂—CH₃ | | X₃—CH₂CH(CH₃)₂ (isobutyl) | X₄—O—CH₃ | X₅-cyclohexyl-N-morpholine | 182 |
| 212 | | | X₁—CH₃ | X₂—CH₃ | | X₃—CH₂CH(CH₃)₂ (isobutyl) | X₄—O—CH₃ | X₅-cyclohexyl-N-piperazine-N-CH₂-cyclopropyl | 187 |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 213 | | H | | X₂—CH₃ | R | X₃—cyclohexyl | X₄—O—CH₃ | X₅—trans-cyclohexyl-N(piperazine)-N-C(O)CH₃ | 248 |
| 214 | | H | | X₂—CH₂CH₃ | R | X₃—CH(CH₃)₂ | X₄—O—CH₃ | X₅—trans-cyclohexyl-N(piperazine)-N-CH₃ | 338 |
| 215 | | | X₁—CH₃ | X₂—CH₃ | | X₃—CH₂CH(CH₃)₂ | X₄—O—CH₃ | X₅—trans-cyclohexyl-N(piperazine)-N-CH₃ | 232 |
| 216 | | H | | X₂—CH₃ | R | X₃—cyclohexyl | X₄—O—CH₃ | X₅—trans-cyclohexyl-N(piperazine)-N-CH₃ | 217 |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 217 | | H | | X₂—CH₃ | R | X₃-cyclopentyl | X₄-O-CH₃ | X₅-cyclohexyl-N(piperazine-N-CH₃) | 139 |
| 218 | | H | | X₂⬩CH₃ | R | X₃-CH₂CH(CH₃)CH₃ (isobutyl) | X₄-O-CH₃ | X₅-cyclohexyl-N(thiomorpholine) | |
| 219 | | H | | X₂—CH₃ | R | X₃-CH₂CH(CH₃)CH₃ | X₄-O-CH₃ | X₅-cyclohexyl-N(morpholine) | 298 |
| 220 | | H | | X₂⬩CH₃ | R | X₃-CH₂C(CH₃)₃ | X₄-O-CH₃ | X₅-cyclohexyl-N(morpholine) | 279 |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 221 | | | H | X₂◂CH₃ | R | X₃-CH₂CH(CH₃)CH₃ | X₄-O-CH₃ | X₅-cyclohexyl-N(piperazine)-N-CH₃ | 336 |
| 222 | | | H | X₂-CH₂CH₃ | R | X₃-CH₂CH(CH₃)CH₃ | X₄-O-CH₃ | X₅-cyclohexyl-N(piperazine)-N-CH₃ | 241 |
| 223 | | 1 | H | X₂◂CH₃ | R | X₃-phenyl | CH₃CH₂-O-X₄ | X₅-piperidine-N-CH₃ | |
| 224 | 1.056 | 1 | H | X₂◂CH₃ | R | X₃-(3-methoxyphenyl) | CH₃-O-X₄ | X₅-piperidine-N-CH₃ | |
| 225 | 1.18 | 1 | H | X₂◂CH₃ | R | X₃-(3-methoxyphenyl) | H | X₅-piperidine-N-CH₃ | |

TABLE 1-continued
| Example | HELA | H460-VINC | R¹ | R² | Config. R¹ or R² | R³ | R⁴ | Lₙ—R⁵ₘ | m.p |
|---------|------|-----------|-----|-----|------|-----|-----|---------|-----|
| 226 | 0.295 | 1 | H | X₂—CH₃ | R | 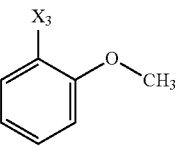 | 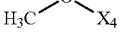 | 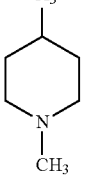 | |
| 227 | 0.853 | 0.946 | H | X₂—CH₃ | R | 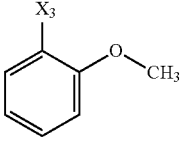 | 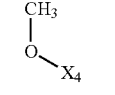 | 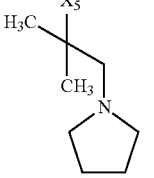 | |
| 228 | | 1 | H | X₂—CH₃ | R | 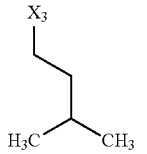 | 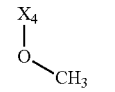 | 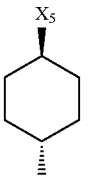 | |
| 229 | | 0.381 | H | X₂—CH₂—CH₃ | R | 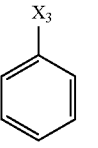 | 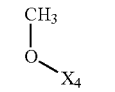 | 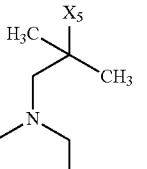 | |
| 230 | | 0.193 | H | X₂—CH₃ | R | 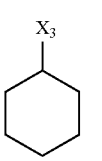 | 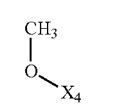 | 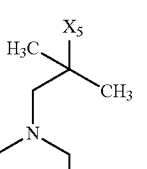 | |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 231 | | 0.17 | H | X₂—CH₃ (wedge) | R | X₃-cyclopentyl | CH₃-O-X₄ | H₃C-C(CH₃)₂-CH₂-N(piperidine)-X₅ | |
| 232 | | 1 | H | X₂—CH₃ (dashed) | R | X₃-cyclohexyl | X₄-O-CH₃ | X₅-cyclohexyl-N(piperazine) | |
| 233 | | | H | X₁—CH₃ (dashed) | R | X₃-CH₂-C(CH₃)₃ | X₄-O-CH₃ | X₅-cyclohexyl-N(2,6-dimethylmorpholine) | |
| 234 | | | H | X₁—CH₂CH₃ | R | X₃-CH(CH₃)₂ | X₄-O-CH₃ | X₅-cyclohexyl-N(2,6-dimethylmorpholine) | |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 235 | | | H | X₁—CH₃ | R | X₃—CH₂CH₂CH(CH₃)₂ | X₄—O—CH₃ | X₅-cyclohexyl-thiomorpholine S-oxide | |
| 236 | | | H | X₁—CH₃ | R | X₃—CH₂CH₂CH(CH₃)₂ | X₄—O—CH₃ | X₅-cyclohexyl-thiomorpholine S-oxide | |
| 237 | 0.012 | 1 | H | X₁—CH₂CH₃ | R | X₃—CH(CH₃)₂ | CH₃—O—X₄ | X₅-piperidine | |
| 238 | 0.015 | 1 | H | X₁—CH₃ | R | X₃-cyclopentyl | CH₃—O—X₄ | X₅-piperidine | |
| 239 | 0.051 | 0.07 | H | X₁—CH₂CH₃ | R | X₃-cyclopentyl | CH₃—O—X₄ | H₃C-C(CH₃)₂-CH₂-morpholine (X₅) | |

TABLE 1-continued

| Example | HELA | H460-VINC | R¹ | R² | Config. R¹ or R² | R³ | R⁴ | Lₙ—R⁵ₘ | m.p |
|---|---|---|---|---|---|---|---|---|---|
| 240 | 0.017 | 0.054 | H | X₁–CH₃ (wedge) | R | cyclohexyl-X₃ | CH₃–O–X₄ | X₅–C(CH₃)₂–CH₂–N(CH₃)₂ | |
| 241 | 0.044 | 0.093 | H | X₁–CH₃ | R | isobutyl-X₃ | CH₃–O–X₄ | X₅–C(CH₃)₂–CH₂–(4-methylpiperazin-1-yl) | |
| 242 | 0.019 | 0.524 | H | X₁–CH₃ | R | isobutyl-X₃ | CH₃–O–X₄ | X₅–CH₂CH₂–piperidin-1-yl | |
| 243 | 0.018 | 0.975 | H | X₁–CH₃ | R | isobutyl-X₃ | CH₃–O–X₄ | X₅–(CH₂)₃–N(CH₃)₂ | |
| 244 | 0.0115 | | H | X₁–CH₃ | R | isobutyl-X₃ | CH₃–O–X₄ | X₅–(CH₂)₃–(4-methylpiperazin-1-yl) | |

As has been found, the compounds of general formula (I) are characterised by their wide range of applications in the therapeutic field. Particular mention should be made of those applications in which the inhibition of specific cell cycle kinases, particularly the inhibiting effect on the proliferation of cultivated human tumour cells but also the proliferation of other cells, such as endothelial cells, for example, plays a part.

As could be demonstrated by FACS analysis, the inhibition of proliferation brought about by the compounds according to the invention is mediated by the arrest of the cells, particularly at the G2/M phase of the cell cycle. The cells arrest, independently of the cells used, for a specific length of time in this phase of the cell cycle before programmed cell death is initiated. An arrest in the G2/M phase of the cell cycle is triggered, for example, by the inhibition of specific cell cycle kinases. Studies in model organisms such as *Schizosaccharomyces pombe* or *Xenopus*, or investigations in human cells have shown that the transition from the G2 phase to mitosis is regulated by the CDK1/cyclin B kinase (Nurse, 1990). This kinase, which is also known as the "mitosis promoting factor" (MPF), phosphorylates and thereby regulates a number of proteins, such as e.g. nuclear lamins, kinesin-like motor proteins, condensins and Golgi matrix proteins, which play an important part in the breakdown of the nuclear envelope, in centrosome separation, the formation of the mitotic spindle apparatus, chromosome condensation and the breakdown of the Golgi apparatus (Nigg. E., 2001). A murine cell line with a temperature-sensitive CDK1 kinase mutant shows a rapid breakdown of the CDK1 kinase and a subsequent arrest in the G2/M phase after a temperature increase (Th'ng et al., 1990). The treatment of human tumour cells with inhibitors against CDK1/cyclin B such as e.g. butyrolactone also leads to an arrest in the G2/M phase and subsequent apoptosis (Nishio, et al. 1996). Another kinase which is involved in the G2 and mitosis phase is polo-like kinase 1 (Plk1), which is responsible for the maturation of the centrosomes, for the activation of the phosphatase Cdc25C, as well as for the activation of the anaphase promoting complex (Glover et al., 1998, Qian, et al., 2001). The injection of Plk1 antibodies leads to a G2 arrest in untransformed cells whereas tumour cells arrest in the mitosis phase (Lane and Nigg, 1996). In addition, the protein kinase aurora B has been described as having an essential function during entry into mitosis. Aurora B phosphorylates histone H3 at Ser11 and thereby initiates chromosome condensation (Hsu, J. Y. et al., 2000). A specific cell cycle arrest in the G2/M phase may, however, also be triggered e.g. by the inhibition of specific phosphatases such as e.g. Cdc25C (Russell and Nurse, 1986). Yeasts with a defective cdc25 gene arrest in the G2 phase, while overexpression of cdc25 leads to early entry into the mitosis phase (Russell and Nurse, 1987). However, an arrest in the G2/M phase can also be triggered by the inhibition of certain motor proteins, so-capped kinesins such as e.g. Eg5 (Mayer et al., 1999), or by agents which stabilise or destabilise microtubules (e.g. colchicin, taxol, etoposide, vinblastin, vincristin) (Schiff and Horwitz, 1980).

In view of their biological properties the compounds of general formula I according to the invention, their isomers and their physiologically acceptable salts are suitable for the treatment of diseases characterised by excessive or abnormal cell proliferation.

Such diseases include, for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphoma and solid tumours; skin diseases (e.g. psoriasis); bone diseases; cardiovascular diseases (e.g. restenosis and hypertrophy). They are also suitable for protecting proliferating cells (e.g. hair, intestinal, blood and progenitor cells) from damage to their DNA caused by radiation, UV treatment and/or cytostatic treatment (Davis et al., 2001).

The new compounds may be used for the prevention, short-term or long-term treatment of the abovementioned diseases, also in combination with other active substances used for the same indications, e.g. cytostatics.

The activity of the compounds according to the invention was determined in the cytotoxicity test on cultivated human tumour cells and/or in a FACS analysis, for example on HeLaS3 cells. In both test methods, the compounds exhibited a good to very good activity, i.e. for example an $EC_{50}$ value in the HeLaS3 cytotoxicity test of less than 5 µmol, generally less than 1 µmol.

Measurement of Cytotoxicity on Cultivated Human Tumour Cells

To measure the cytotoxicity on cultivated human tumour cells, cells of the cervical cancer tumour cell line HeLaS3 (obtained from American Type Culture Collection (ATCC)) in Ham's F12 Medium (Life Technologies) and 10% foetal calf serum (Life Technologies) were cultivated and harvested in the logarithmic growth phase. Then the HeLaS3 cells were placed in 96-well plates (Costar) at a density of 1000 cells per well and incubated overnight in an incubator (at 37° C. and 5% $CO_2$), while on each plate 6 wells were filled only with medium (3 wells as a control of the medium, 3 wells for incubation with reduced AlamarBlue). The active substances were added to the cells in various concentrations (dissolved in DMSO; final concentration: 1%) (in each case as a triple measurement). After 72 hours' incubation, 20 µl of Alamar-Blue (AccuMed International) were added to each well, and the cells were incubated for a further 7 hours. As a control, 20 µl of reduced Alamar Blue (AlamarBlue reagent which had been autoclaved for 30 min) were added to 3 wells. After 7 h incubation the colour change of the AlamarBlue reagent in the individual wells was determined in a Perkin Elmer fluorescence spectrophotometer (excitation 530 nm, emission 590 nm, slits 15, integrate time 0.1). The amount of Alamar-Blue reagent reacted represents the metabolic activity of the cells. The relative cell activity was calculated as a percentage of the control (HeLa S3 cells without inhibitor) and the active substance concentration which inhibits the cell activity by 50% ($IC^{50}$) was obtained. The values were calculated from the average of three individual measurements, correcting for the control value (medium control).

FACS Analysis

Propidium iodide (PI) binds stoichiometrically to double-stranded DNA, and is thus suitable for determining the percentage of cells in the G1, S and G2/M phase of the cell cycle on the basis of the cell DNA content. Cells in the G0 and G1 phase have a diploid DNA content (2N), whereas cells in G2 or mitosis have a 4N DNA content.

For PI staining, 0.4 million HeLaS3 cells were seeded, for example, on a 75 cm² cell culture flask, and after 24 h either 1% DMSO was added as control or the substance was added in various concentrations (in 1% DMSO). The cells were incubated for 24 h with the substance or with DMSO, before the cells were washed with 2×PBS and detached with trypsin/EDTA. The cells were centrifuged (1000 rpm, 5 min, 4° C.), and the cell pellet was washed 2× with PBS, before the cells were resuspended in 0.1 ml of PBS. Then the cells were fixed with 80% ethanol for 16 hours at 4° C. or alternatively for 2 hours at −20° C. The fixed cells ($10^6$ cells) were centrifuged (1000 rpm, 5 min, 4° C.), washed with PBS and then centrifuged again. The cell pellet was resuspended in 2 ml of Triton X-100 in 0.25% PBS, and incubated for 5 min on ice, before 5 ml of PBS were added and the mixture was centrifuged again. The cell pellet was resuspended in 350 µl of PI stain solution (0.1 mg/ml of Raze A, 10 µg/ml of presidium iodide in 1×PBS). The cells were incubated for 20 min in the dark with the stain buffer before being transferred into sample measuring vessels for the FACS scan. The DNA measurement was carried out in a Becton Dickinson FACS Analyzer, with an argon laser (500 mW, emission 488 nm), and the DNA Cell Quest Program (BD). The logarithmic PI fluorescence was determined with a band-pass filter (BP 585/42). The cell populations in the individual phases of the cell cycle were quantified with the ModFit LT program of Becton Dickinson.

The compounds of general formula (I) may be used on their own or combined with other active substances according to the invention, optionally also in conjunction with other pharmacologically active substances. Suitable preparations include for example tablets, capsules, suppositories, solutions, particularly solutions for injection (s.c., i.v., i.m.) and infusion, syrups, emulsions or dispersible powders. The amount of pharmaceutically active compound in each case should be in the range from 0.1-90 wt. %, preferably 0.5-50 wt. % of the total composition, i.e. in amounts which are sufficient to achieve the dosage range given below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharin, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of preservatives such as p-hydroxybenzoates, or stabilisers such as alkali metal salts of ethylenediamine tetraacetic acid, optionally using emulsifiers and/or dispersants, while if water is used as the diluent organic solvents may optionally be used as solubilisers or auxiliary solvents, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Suitable excipients may be, for example, water, pharmaceutically acceptable organic solvents, such as paraffins (e.g. petroleum fractions), oils of vegetable origin (e.g. groundnut or sesame oil), mono- or polyfunctional alcohols (e.g. ethanol or glycerol), carriers such as e.g. natural mineral powders (e.g. kaolin, clays, talc, chalk), synthetic mineral powders (e.g. highly dispersed silica and silicates), sugar (e.g. glucose, lactose and dextrose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered in the usual way, preferably by oral or transdermal route, particularly preferably by oral route. When administered orally the tablets may, of course, contain additives, such as e.g. sodium citrate, calcium carbonate and dicalcium phosphate together with various additives, such as starch, preferably potato starch, gelatine and the like, in addition to the abovementioned carriers. Lubricants such as magnesium stearate, sodium laurylsulphate and talc may also be used to form tablets. In the case of aqueous suspensions the active substances may be combined with various flavour enhancers or colourings in addition to the abovementioned excipients.

For parenteral use, solutions of the active substances may be prepared using suitable liquid carrier materials.

The dosage for intravenous use is 1-1000 mg per hour, preferably between 5-500 mg per hour.

However, it may optionally be necessary to deviate from the amounts specified, depending on the body weight or method of administration, the individual response to the medication, the nature of the formulation used and the time or interval over which it is administered. Thus, in some cases, it may be sufficient to use less than the minimum quantity specified above, while in other cases the upper limit specified will have to be exceeded. When large amounts are administered it may be advisable to spread them over the day in a number of single doses.

The formulation examples that follow illustrate the present invention without restricting its scope:

Examples of Pharmaceutical Formulations

| A) | Tablets | per tablet |
|---|---|---|
| | active substance | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance | 80 mg |
| | lactose | 55 mg |
| | corn starch | 190 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) | Ampoule solution | |
|---|---|---|
| | active substance | 50 mg |
| | sodium chloride | 50 mg |
| | water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

What is claimed is:

1. A compound of formula (I) as shown in the following Table

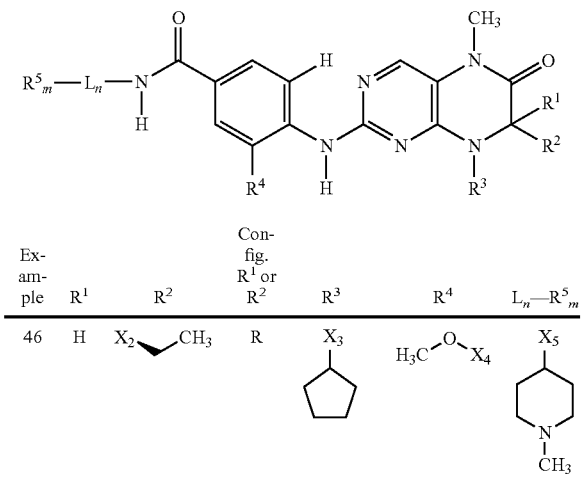

| Example | $R^1$ | $R^2$ | Config. $R^1$ or $R^2$ | $R^3$ | $R^4$ | $L_n$—$R^5_m$ |
|---|---|---|---|---|---|---|
| 46 | H | $X_2$⤳$CH_3$ | R | $X_3$⬠ | $H_3C$—O—$X_4$ | $X_5$ piperidine-N-$CH_3$ | or a pharmacologically acceptable acid addition salt thereof, wherein the abbreviations $X_2$, $X_3$, $X_4$ and $X_5$ used in the Table in each case denote a link to a position in the general formula shown under the Table instead of the corresponding groups $R^2$, $R^3$, $R^4$ and L-$R^5$.

* * * * *